(12) United States Patent
Whalley et al.

(10) Patent No.: US 12,357,586 B2
(45) Date of Patent: Jul. 15, 2025

(54) USE OF THE PHYTOCANNABINOID CANNABIDIOL (CBD) IN COMBINATION WITH A STANDARD ANTI-EPILEPTIC DRUG (SAED) IN THE TREATMENT OF EPILEPSY

(71) Applicant: JAZZ PHARMACEUTICALS RESEARCH UK LIMITED, Sittingbourne (GB)

(72) Inventors: Benjamin Whalley, Reading (GB); Claire Williams, Reading (GB); Gary Stephens, Reading (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 0 days.

(21) Appl. No.: 17/585,415

(22) Filed: Jan. 26, 2022

(65) Prior Publication Data
US 2022/0395470 A1  Dec. 15, 2022

Related U.S. Application Data

(63) Continuation of application No. 13/977,766, filed as application No. PCT/GB2012/050002 on Jan. 3, 2012, now abandoned.

(30) Foreign Application Priority Data

Jan. 4, 2011 (GB) ..................................... 1100043

(51) Int. Cl.
| | |
|---|---|
| A61K 31/05 | (2006.01) |
| A61K 31/19 | (2006.01) |
| A61K 31/352 | (2006.01) |
| A61K 31/4015 | (2006.01) |
| A61K 31/515 | (2006.01) |
| A61K 36/00 | (2006.01) |
| A61K 45/06 | (2006.01) |

(52) U.S. Cl.
CPC .............. *A61K 31/05* (2013.01); *A61K 31/19* (2013.01); *A61K 31/352* (2013.01); *A61K 31/4015* (2013.01); *A61K 31/515* (2013.01); *A61K 36/00* (2013.01); *A61K 45/06* (2013.01)

(58) Field of Classification Search
CPC ....................................................... A61K 31/05
See application file for complete search history.

(56) References Cited

U.S. PATENT DOCUMENTS

| | | |
|---|---|---|
| 6,403,126 B1 | 6/2002 | Webster |
| 6,730,330 B2 | 5/2004 | Whittle et al. |
| 6,946,150 B2 | 9/2005 | Whittle |
| 6,949,582 B1 | 9/2005 | Wallace |
| 7,968,594 B2 | 6/2011 | Guy et al. |
| 8,293,786 B2 | 10/2012 | Stinchcomb |
| 8,632,825 B2 | 1/2014 | Diez et al. |
| 8,673,368 B2 | 3/2014 | Guy et al. |
| 8,790,719 B2 | 7/2014 | Parolaro et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Guy et al. |
| 9,259,449 B2 | 2/2016 | Raderman |
| 9,522,123 B2 | 2/2016 | Whallev et al. |
| 9,474,726 B2 | 10/2016 | Guy et al. |
| 9,669,002 B2 | 6/2017 | Guy et al. |
| 9,730,911 B2 | 8/2017 | Verzura et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 9,962,341 B2 | 5/2018 | Stott et al. |
| 10,039,724 B2 | 8/2018 | Stott et al. |
| 10,092,525 B2 | 10/2018 | Guy et al. |
| 10,098,867 B2 | 10/2018 | Javid et al. |

(Continued)

FOREIGN PATENT DOCUMENTS

| | | |
|---|---|---|
| CA | 2737447 A1 | 10/2012 |
| CA | 2859934 A1 | 3/2016 |

(Continued)

OTHER PUBLICATIONS

[No Author Listed] "Cannabidiol for Aicardi Syndrome," Salutaris., Retrieved on Feb. 10, 2017, Retrieved from the internet: URL <https://web.archive.org/web/20141012220050/http://salutarisdrops.com/cannabidiol-aicardi-syndrome/>, © 2014, 3 pages.

[No Author Listed] "GW Pharmaceuticals Provides Update on Orphan Program in Childhood Epilepsy for Epidiolex®," GW Phann., Available online Nov. 14, 2013, Retrieved Feb. 10, 2017, Retrieved from the internet: URL <http://wv:w.gwphann.com/GW%20Phannaceuticals%20Provides%20Update%20on%20rphan%20Program%20in%20Childhoocl%20Epilepsy%20for%120Epidiolex.aspx>, 5 pages.

(Continued)

Primary Examiner — Yong S. Chong
(74) Attorney, Agent, or Firm — COOLEY LLP

(57) ABSTRACT

The invention relates to the use of cannabidiol (CBD), at a dose of greater than 300 mg/day, in combination with a standard anti-epileptic drug (SAED) which acts via sodium or calcium channels, for use in the treatment of epilepsy. The SAED is preferably one which •modities low-threshold or transient neuronal calcium currents, or •reduces high-frequency neuronal firing and sodium-dependent action potentials and enhances GABA effects. Preferred SAEDs are ethosuximide and valproate.

12 Claims, 5 Drawing Sheets

(56) References Cited

U.S. PATENT DOCUMENTS

| | | |
|---|---|---|
| 10,111,840 B2 | 10/2018 | Guy et al. |
| 10,137,095 B2 | 11/2018 | Guy et al. |
| 10,220,005 B2 | 3/2019 | Martinez-Orgado |
| 10,226,433 B2 | 3/2019 | DiMarzo et al. |
| 10,583,096 B2 | 3/2020 | Guy et al. |
| 10,603,288 B2 | 3/2020 | Guy et al. |
| 10,653,641 B2 | 5/2020 | Robson et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,758,514 B2 | 9/2020 | Liu et al. |
| 10,765,643 B2 | 9/2020 | Guy et al. |
| 10,799,467 B2 | 10/2020 | Whalley et al. |
| 10,807,777 B2 | 10/2020 | Whittle |
| 10,849,860 B2 | 12/2020 | Guy et al. |
| 10,918,608 B2 | 2/2021 | Guy et al. |
| 10,966,939 B2 | 4/2021 | Guy et al. |
| 11,000,486 B2 | 5/2021 | Wright et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,154,516 B2 | 10/2021 | Guy et al. |
| 11,154,517 B2 | 10/2021 | Wright et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 11,291,631 B2 | 4/2022 | Shah |
| 11,311,498 B2 | 4/2022 | Guy et al. |
| 11,318,109 B2 | 5/2022 | Whalley et al. |
| 11,357,741 B2 | 6/2022 | Guy et al. |
| 11,400,055 B2 | 8/2022 | Guy et al. |
| 11,406,623 B2 | 8/2022 | Guy et al. |
| 11,413,266 B2 | 8/2022 | Biro et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 11,679,087 B2 | 6/2023 | Guy et al. |
| 11,701,330 B2 | 7/2023 | Guy et al. |
| 11,766,411 B2 | 9/2023 | Guy et al. |
| 11,793,770 B2 | 10/2023 | Stott et al. |
| 11,806,319 B2 | 11/2023 | Wilkhu et al. |
| 11,865,102 B2 | 1/2024 | Guy et al. |
| 11,963,937 B2 | 4/2024 | Guy et al. |
| 2002/0137064 A1 | 9/2002 | Desprez et al. |
| 2003/0021752 A1* | 1/2003 | Whittle ............... A61K 9/0031 424/45 |
| 2003/0158191 A1 | 8/2003 | Travis |
| 2003/0166727 A1 | 9/2003 | Mechoulam et al. |
| 2004/0039048 A1 | 2/2004 | Guzman Pastor et al. |
| 2004/0049059 A1 | 3/2004 | Mueller |
| 2004/0110828 A1 | 6/2004 | Chowdhury et al. |
| 2004/0138293 A1 | 7/2004 | Werner et al. |
| 2005/0042172 A1 | 2/2005 | Whittle |
| 2005/0165259 A1 | 7/2005 | Martin |
| 2005/0266108 A1 | 12/2005 | Flockhart et al. |
| 2006/0039959 A1 | 2/2006 | Wessling |
| 2006/0234273 A1 | 10/2006 | Desprez et al. |
| 2006/0247304 A1 | 11/2006 | Guy et al. |
| 2007/0060638 A1 | 3/2007 | Olmstead |
| 2007/0072938 A1 | 3/2007 | Rose |
| 2007/0203249 A1 | 8/2007 | Cercietti et al. |
| 2008/0057117 A1 | 3/2008 | Werner et al. |
| 2008/0119544 A1 | 5/2008 | Guy et al. |
| 2008/0188461 A1 | 8/2008 | Guan |
| 2008/0262099 A1 | 10/2008 | Whittle et al. |
| 2009/0264063 A1 | 10/2009 | Tinsley et al. |
| 2009/0306221 A1 | 12/2009 | Guy et al. |
| 2010/0204312 A1 | 8/2010 | McAllister et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2011/0086113 A1 | 4/2011 | Velasco Diez et al. |
| 2011/0117216 A1 | 5/2011 | Velasco Diez et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0225136 A1 | 9/2012 | Whittle et al. |
| 2012/0270845 A1 | 10/2012 | Bannister et al. |
| 2013/0059018 A1 | 3/2013 | Parolaro et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0287067 A1 | 9/2014 | Velasco Diez et al. |
| 2014/0335208 A1 | 11/2014 | Cawthorne et al. |
| 2014/0343044 A1 | 11/2014 | Ceulemens |
| 2015/0086653 A1 | 3/2015 | Parolaro et al. |
| 2015/0111939 A1 | 4/2015 | Gruening et al. |
| 2015/0181924 A1 | 7/2015 | Llamas |
| 2015/0313867 A1 | 11/2015 | Velasco Diez et al. |
| 2015/0320698 A1 | 11/2015 | Whalley et al. |
| 2015/0335590 A1 | 11/2015 | Whalley et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0136127 A1 | 5/2016 | Liu et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2019/0099492 A1 | 4/2019 | Velasco Diez et al. |
| 2019/0167583 A1 | 6/2019 | Shah et al. |
| 2019/0175547 A1 | 6/2019 | Stott et al. |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0069333 A1 | 3/2021 | Velasco Diez et al. |
| 2021/0100755 A1 | 4/2021 | Whalley et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0308072 A1 | 10/2021 | Wright et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |

(56) References Cited

U.S. PATENT DOCUMENTS

| | | | |
|---|---|---|---|
| 2022/0040155 | A1 | 2/2022 | Guy et al. |
| 2022/0062197 | A1 | 3/2022 | Stott et al. |
| 2022/0062211 | A1 | 3/2022 | Stott et al. |
| 2022/0087951 | A1 | 3/2022 | Guy et al. |
| 2022/0096397 | A1 | 3/2022 | Wright et al. |
| 2022/0168266 | A1 | 6/2022 | Guy et al. |
| 2022/0183997 | A1 | 6/2022 | Guy et al. |
| 2022/0184000 | A1 | 6/2022 | Guy et al. |
| 2022/0202738 | A1 | 6/2022 | Guy et al. |
| 2022/0211629 | A1 | 7/2022 | Wilkhu et al. |
| 2022/0226257 | A1 | 7/2022 | Guy et al. |
| 2022/0233495 | A1 | 7/2022 | Silcock et al. |
| 2022/0249396 | A1 | 8/2022 | Guy et al. |
| 2022/0257529 | A1 | 8/2022 | Guy et al. |
| 2022/0265573 | A1 | 8/2022 | Guy et al. |
| 2022/0288055 | A1 | 9/2022 | Silcock et al. |
| 2022/0362149 | A1 | 11/2022 | Shah |
| 2022/0378715 | A1 | 12/2022 | Guy et al. |
| 2022/0378738 | A1 | 12/2022 | Guy et al. |
| 2022/0387347 | A1 | 12/2022 | Whalley et al. |
| 2022/0395471 | A1 | 12/2022 | Guy et al. |
| 2023/0000789 | A1 | 1/2023 | Guy et al. |
| 2023/0022487 | A1 | 1/2023 | Guy et al. |
| 2023/0024312 | A1 | 1/2023 | Whalley et al. |
| 2023/0026079 | A1 | 1/2023 | Guy et al. |
| 2023/0038423 | A1 | 2/2023 | Silcock et al. |
| 2023/0068885 | A1 | 3/2023 | Guy et al. |
| 2023/0143812 | A1 | 5/2023 | Knappertz et al. |
| 2023/0235825 | A1 | 7/2023 | Thompson et al. |
| 2023/0248664 | A1 | 8/2023 | Guy et al. |
| 2023/0263744 | A1 | 8/2023 | Guy et al. |
| 2023/0277560 | A1 | 9/2023 | Checketts et al. |
| 2023/0277561 | A1 | 9/2023 | Checketts et al. |
| 2023/0277562 | A1 | 9/2023 | Checketts et al. |
| 2023/0277563 | A1 | 9/2023 | Checketts et al. |
| 2023/0285419 | A1 | 9/2023 | Checketts et al. |
| 2023/0285420 | A1 | 9/2023 | Checketts et al. |
| 2023/0285421 | A1 | 9/2023 | Checketts et al. |
| 2023/0285422 | A1 | 9/2023 | Checketts et al. |
| 2023/0285423 | A1 | 9/2023 | Checketts et al. |
| 2023/0285424 | A1 | 9/2023 | Checketts et al. |
| 2023/0285425 | A1 | 9/2023 | Checketts et al. |
| 2023/0285426 | A1 | 9/2023 | Checketts et al. |
| 2023/0285427 | A1 | 9/2023 | Checketts et al. |
| 2023/0285428 | A1 | 9/2023 | Checketts et al. |
| 2023/0301934 | A1 | 9/2023 | Whalley et al. |
| 2023/0301936 | A1 | 9/2023 | Guy et al. |
| 2023/0310464 | A1 | 10/2023 | Checketts et al. |
| 2023/0346809 | A1 | 11/2023 | Craig et al. |
| 2023/0372367 | A1 | 11/2023 | Checketts et al. |
| 2023/0372368 | A1 | 11/2023 | Checketts et al. |
| 2024/0016819 | A1 | 1/2024 | Craig et al. |
| 2024/0025858 | A1 | 1/2024 | Silcock et al. |
| 2024/0033229 | A1 | 2/2024 | Guy et al. |
| 2024/0033272 | A1 | 2/2024 | Checketts et al. |
| 2024/0043388 | A1 | 2/2024 | Silcock et al. |
| 2024/0050452 | A1 | 2/2024 | Craig et al. |
| 2024/0091241 | A1 | 4/2024 | Guy et al. |
| 2024/0130981 | A1 | 4/2024 | Wilkhu et al. |
| 2024/0131041 | A1 | 4/2024 | Tse et al. |
| 2024/0165048 | A1 | 5/2024 | Guy et al. |

FOREIGN PATENT DOCUMENTS

| | | |
|---|---|---|
| CN | 1976690 A | 6/2007 |
| CN | 101040855 A | 9/2007 |
| CN | 103110582 A | 5/2013 |
| DE | 102012105063 A1 | 12/2013 |
| EP | 1 177 790 A1 | 2/2002 |
| EP | 1 802 274 B1 | 9/2008 |
| EP | 2448637 B1 | 5/2012 |
| GB | 2380129 A | 4/2003 |
| GB | 2384707 A | 8/2003 |
| GB | 2386322 A | 9/2003 |
| GB | 2391865 A | 2/2004 |
| GB | 2418612 A | 4/2006 |
| GB | 2434097 A | 7/2007 |
| GB | 2434312 A | 7/2007 |
| GB | 2439393 A | 12/2007 |
| GB | 2448535 A | 10/2008 |
| GB | 2450753 A | 1/2009 |
| GB | 911580.9 | 7/2009 |
| GB | 2456183 A | 7/2009 |
| GB | 2460672 A | 12/2009 |
| GB | 2471523 A | 1/2011 |
| GB | 2471987 A | 1/2011 |
| GB | 2478595 A | 9/2011 |
| GB | 2479153 A | 10/2011 |
| GB | 2485291 A | 5/2012 |
| GB | 2471565 B | 7/2012 |
| GB | 2487183 A | 7/2012 |
| GB | 2478072 B | 12/2012 |
| GB | 2478074 B | 12/2012 |
| GB | 2492487 A | 1/2013 |
| GB | 2487712 A | 10/2015 |
| GB | 2531282 A | 4/2016 |
| GB | 2438682 A | 12/2017 |
| KR | 2012-0080675 A | 7/2012 |
| WO | WO 01/58445 A1 | 8/2001 |
| WO | WO 01/87295 A1 | 11/2001 |
| WO | WO-2002064109 A2 | 8/2002 |
| WO | WO 2002/069993 A1 | 9/2002 |
| WO | WO 2003/063847 A1 | 8/2003 |
| WO | WO-2003099302 A1 | 12/2003 |
| WO | WO-2004016246 A1 | 2/2004 |
| WO | WO-2004016277 A2 | 2/2004 |
| WO | WO 2004/041269 A2 | 5/2004 |
| WO | WO 2005/120478 A1 | 12/2005 |
| WO | WO 2006/037981 A1 | 4/2006 |
| WO | WO-2006054057 A2 | 5/2006 |
| WO | WO 2006/107903 A2 | 10/2006 |
| WO | WO-2006133941 A2 | 12/2006 |
| WO | WO 2007/052013 A1 | 5/2007 |
| WO | WO-2007083098 A1 | 7/2007 |
| WO | WO-2007138322 A1 | 12/2007 |
| WO | WO-2008019146 A2 | 2/2008 |
| WO | WO-2008094181 A3 | 8/2008 |
| WO | WO-2008129258 A1 | 10/2008 |
| WO | WO-2008144475 A1 | 11/2008 |
| WO | WO-2008021394 A3 | 12/2008 |
| WO | WO-2008146006 A1 | 12/2008 |
| WO | WO-2009007697 A1 | 1/2009 |
| WO | WO-2009007698 A1 | 1/2009 |
| WO | WO 2009/147438 A1 | 12/2009 |
| WO | WO 2009/147439 A1 | 12/2009 |
| WO | WO-2009020666 A1 | 12/2009 |
| WO | WO 2010/012506 A1 | 2/2010 |
| WO | WO-2011001169 A1 | 1/2011 |
| WO | WO-2011121351 A1 | 10/2011 |
| WO | WO-2012033478 A1 | 3/2012 |
| WO | WO-2012093255 A1 | 7/2012 |
| WO | WO-2013032351 A1 | 3/2013 |
| WO | WO 2013/045891 A1 | 4/2013 |
| WO | WO-2014146699 A1 | 9/2014 |
| WO | WO-2015142501 A1 | 9/2015 |
| WO | WO 2015/198078 A | 12/2015 |
| WO | WO-2015184127 A2 | 12/2015 |
| WO | WO-2015193667 A1 | 12/2015 |
| WO | WO-2015193668 A1 | 12/2015 |
| WO | WO 2016/059404 A1 | 4/2016 |
| WO | WO-2016059405 A1 | 4/2016 |
| WO | WO 2016/087649 A2 | 6/2016 |
| WO | WO-2016084075 A1 | 6/2016 |
| WO | WO-2016118391 A1 | 7/2016 |
| WO | WO-2016147186 A1 | 9/2016 |
| WO | WO-2016022936 A1 | 11/2016 |
| WO | WO-2016199148 A1 | 12/2016 |
| WO | WO-2017168138 A1 | 10/2017 |
| WO | WO-2018002636 A1 | 1/2018 |
| WO | WO-2018002637 A1 | 1/2018 |
| WO | WO-2018037203 A1 | 3/2018 |

(56) References Cited

OTHER PUBLICATIONS

[No Author Listed] "GW Pharmaceuticals Receives Orphan Drug Designation by FDA for Epidiolex@ in the Treatment of Lennox-Gastaut Syndrome," GW Phann., Available online Feb. 28, 2014, Retrieved Feb. 10, 2017, Retrieved from the internet: URL https:i/www.gwpharm.com/about-us/newsigw-pharmaceuticals-receives-orphan-drug-designation-fda-epidiolex%C2%AE-treatment-lennox, 4 pages.
[No Author Listed] "Lennox-Gastaut Syndrome," Child Neurology Foundation, available on or before Sep. 6, 2005, retrieved on May 21, 2018, <http://www.childneurologyfoundation.org/disorders/lgs-lennox-gastaut-syndrome>, 10 pages.
[No Author Listed] "Models of Chemically-Induced Acute Seizures," Models of Seizures and Epilepsy, Elsevier, 2006, 127-152.
[No Author Listed] "What are the Highest CBD Strains?" accessed Feb. 16, 2017, available online at www.leafscience.com, published Oct. 15, 2014, 2 pages.
[No Author Listed] Cannabinoid. Wikipedia. Retrieved on Jul. 9, 2015 from https://en.wikipedia.org/wiki/Cannabinoid.
[No Author Listed] Estimating the Maximum Safe Starting Dose in Initial Clinical Trials for Therapeutics in Adult Healthy Volunteers. FDA Guidance for Industry, Jul. 2005.
[No Author Listed] GW Pharmaceuticals Announces Epidiolex Receives Fast Track Designation from FDA for the Treatment of Dravet Syndrome. GW Pharmaceuticals Press Release dated Jun. 6, 2014.
[No Author Listed] GW Pharmaceuticals Announces Physician Reports of Epidiolex Treatment Effect in Children and Young Adults with Treatment-resistant epilepsy from Physician-Led Expanded Access Treatment Program. GW Pharmaceuticals Press Release dated Jun. 17, 2014.
[No Author Listed] Orphan Drug Designation Granted for Epidiolex in Dravet syndrome by the FDA—Seven Expanded Access INDs granted by FDA to US physicians to treat with Epidiolex 125 children suffering from intractable epilepsy syndromes. GW Pharmaceuticals Press Release dated Nov. 14, 2013.
[No Author Listed], "Missouri House passes cannabis extract legislation," Kansas City Star, 2014, https://kansascity .com/news/politics-government/article346747.html, 2 pages.
[No Author Listed], Cover and Table of Contents, J Pharmacology and Exp Therapeutics, Feb. 2010, 332(2), 4 pages.
[No Author Usted] "Convulsive Disorders and Their Interference with Driving," Medicos., Retrieved Feb. 10, 2017, Retrieved from internet: URL <https://www.medicosporlaseguridadvial.com/en/clinical-subjects/neurologic-diseases/convulsive-disorders-and-their-interference-with-driving/>, 2014, 3 pages.
Alger (2006). "Not too excited? Thank your endocannabinoids," Neuron, 51(4):393-395.
American Epilepsy Society, Three Studies Shed New Light on the Effectiveness of Cannabis in Epilepsy, Oct. 14, 2014, 2 pages.
Ames et al., Anticonvulsant effect of cannabidiol. S Afr Med J. Jan. 4, 1986;69(1):14.
Annex to the Communication-Opposition for Application No. I 0734541 .5, dated Jan. 28, 2016, 5 pages.
Arain (2009). "Pregabalin in the management of partial epilepsy," Neuropsychiatr Dis Treat, 2009(5):407-413.
Arslan et al., (2013). "Self-emulsifying Drug Delivery Systems," FABAD J Pharm Sci, 2013(38):55-64.
Arzimanoglou et al., (2011). "All children who experience epileptic falls do not necessarily have Lennox-Gastaut syndrome . . . but many do," Epileptic Disord, 2011(13):S3-S13.
AU Re-examination report—standard patent for Australian Patent No. 2012204800, dated May 3, 2019, 7 pages.
Avoli et al., (2005). "Cellular and molecular mechanisms of epilepsy in the human brain," Prog Neurobiol, 77(3):166-200.
Bakhsh, Miftaah-al-Khazaain. 1930: 607-8. Urdu. Exhibit 3.
Bancaud et al., (1981). "Proposal for Revised Clinical and Electroencephalographic Classification of Epileptic Seizures," Epilepsia, 22(4):489-501.

Banerjee et al., (2006). "Case Report: Aicardi syndrome: A report of five Indian cases," Neurology India, 54(1): 91-93.
Barker-Haliski et al., (2014). "How Clinical Development Can, and Should. Inform Translational Science," Neuron, 84(3):582-593.
Benowitz et al., (1980). "Metabolic and Psychophysiologic studies of cannabidiol hexobarbital interaction," Clin Pharmacol Ther., 28(1):115-120.
Benowitz et al., (1981). "Cardiovascular and metabolic considerations in prolonged cannabinoid administration in man," J Clin Pharm, 21(S1): 214S-223S.
Bertram (2007). "The Relevance of Kindling for Human Epilepsy," Epilepsia, 48(S2):65-74.
Bhatt et al., (2008). "Indigenous plants in traditional healthcare system in Kedarnath valley of western Himalaya," Indian J Tradit Knowl., 7(2):300-310.
Bhattacharyya et al., (2009). "Modulation of mediotemporal and ventrostriatal function in humans by Delta9-tetrahydrocannabinol: a neural basis for the effects of *Cannabis sativa* on learning and psychosis," Arch Gen Psychiatry, 66(4):442-451.
BipolarHealthGroup.org [online], "Charlotte's Web Hemp Remedy," Bipolar Health Group, available on or before Sep. 6, 2017, retrieved on May 21, 2018, URL <http:/bipolarhealthgroup.org/index.php/charlottes-web-hemp-remedy/>, 6 pages.
Booth. "Legalization's opening of medical pot research is dream and nightmare," Denver Post, Dec. 14, 2013.
Bostanci et al., (2006). "The effects of octanol on penicillin induced epileptiform activity in rats: an in vivo study," Epilepsy Res., 71(2-3): 188-194.
Braida et al., (2003). "Post-ischemic treatment with cannabidiol prevents electroencephalographic flattening, hyperlocomotion and neuronal injury in gerbils," Neuroscience Letters, 346(1-2):61-64.
Brust et al., (1992). "Marijuana use and the risk of new onset seizures," Trans Am Clin Climatol Assoc., 103:176-181.
Carlini et al., (1981). "Hypnotic and antiepileptic effects of cannabidiol," J Clin Pharmacol., 21(S1):417S-427S.
Castel-Branco et al., (2009). "The Maximal Electroshock Seizure (MES) Model in the Preclinical Assessment of Potential New Antiepileptic Drugs," Methods Find Exp Clin Pharmacol., 31(2); 101-106.
CDC. "2 to 20 years: Girls Stature-for-age and Weigh-for-age percentiles," National Center for Health Statistics and National Center for Chronic Disease Prevention and Health Promotion, last modified Nov. 2000, <https://www.cdc.gov/growthcharts/data/setlclinical/cj411022.pdf>, 1 page.
Charlotte's Web. "Full Spectrum Phyto-Cannabinoids Outperform Single-Molecule Compounds," CWHemp.com, Jan. 11, 2017, retrieved on Jun. 16, 2017, <https://www.cwhemp.com/blog/whole-plant-cw-hemp-cannabinoids>, 5 pages.
Chiron et al., (2011). "The Pharmacologic Treatment of Dravet Syndrome," Epilepsia, 52(S2):72-75.
Chiu et al., (1979). "The Influence of Cannabidiol and delta9-Tetrahydrocannabinol on Cobalt Epilepsy in Rats," Epilepsia, 20(4):365-375.
Chou (2006). "Theoretical basis, experimental design, and computerized simulation of synergism and antagonism in drug combination studies," Pharmacol Rev., 58(3):621-681.
Combined Search and Examination Report mailed Jan. 4, 2012 for Application No. GBI 116789.7.
Combined Search and Examination Report mailed Mar. 25, 2011 for Application No. GB1100043.7.
Combined Search and Examination Report mailed Sep. 5, 2014 for Application No. GB1414813.4.
Combined Search and Examination Report under Sections 17 and 18(3) for International Application No. GB1410771.8, dated Feb. 27, 2015, 7 pages.
Combined Search and Examination Report under Sections 17 and 18(3) for international Application No. GB1418166.3, dated Jul. 2, 2015, 8 pages.
Combined Search and Examination Report under Sections 17 and 18(3) for International Application No. GB1418171.3, dated Jun. 29, 2015, 8 pages.

(56) References Cited

OTHER PUBLICATIONS

Combined Search and Examination Report under Sections 17 and 18(3) for International Application No. GB1506550. I, dated Feb. 5, 2016, 9 pages.
Combined Search and Examination Report under Sections 17 and 18(3) for International Application No. GBI418170.5, dated Jul. 2, 2015, 6 pages.
Communication of a Notice of Opposition for Application No. 10734541.5, dated Dec. 17, 2014, 1 page.
Communication Pursuant to Article 94(3) EPC in European Patent Application No. 10734541.5, dated Oct. 23, 2012, 3 pages.
Conry et al., (2009). "Clobazam in the treatment of Lennox-Gastaut syndrome," Epilepsia, 50(5):1158-1166.
Consroe et al., (1975). "Anticonvulsant nature of marihuana smoking," JAMA, 234(3):306-307.
Consroe et al., (1977). "Anticonvulsant drug antagonism of delta9tetrahydrocannabinol-induced seizures in rabbits," Res Commun Chem Pathol Pharmacol., 16(1):1-13.
Consroe et al., (1977). "Anticonvulsant interaction of cannabidiol and ethosuximide in rats," J Pharm Pharmacol., 29(1):500-501.
Consroe et al., (1977). "Cannabidiol—antiepileptic drug comparisons and interactions in experimentally induced seizures in rats," J Pharmacol Exp Ther., 201(1):26-32.
Consroe et al., (1982). "Effects of cannabidiol on behavioral seizures caused by convulsant drugs or current in mice," Eur J Pharmacol., 83(3-4):293-298.
Consroe et al., (1991). "Controlled clinical trial of cannabidiol in Huntington's Disease," Pharmacology Biochemistry & Behavior, 40(3):701-708.
Consroe et al., Chapter 12, "Potential Role of Cannabinoids for Therapy of Neurological Disorders," p. 459 in Marijuana/Cannabinoids: Neurobiology and Neurophysiology, ed. L. Murphy (1992).
Consroe et al., Therapeutic Potential of Cannabinoids in Neurological Disorders, Chapter 2, pp. 21-49, Cannabinoids as Therapeutic Agents, R. Mechoulam, ed., CRC Press, Boca Raton (1986).
Cortesi et al., (2007). "Potential therapeutical effects of cannabidiol in children with pharmacoresistant epilepsy," Med Hypotheses, 68(4):920-921.
Cortez et al., Chapter 10 "Pharmacologic Models of Generalized Absence Seizures in Rodents," Models Seizures Enileosv., 111-126, 2006.
Crespel, et al., "Chapter 14: Lennox-Gastaut Syndrome," Epileptic Syndromes in Infancy, Childhood, and Adolescence, 2012, 5th Edition, ed. M. Bureau, 189-216.
Cunha et al., (1980). "Chronic administration of cannabidiol to healthy volunteers and epileptic patients," Pharmacology, 21(3):175-185.
Curia et al., (2008). "The pilocaipine model of temporal lobe epilepsy," J Neuroscience Methods, 172(2):143-157.
Czapinski et al., (1997). "Randomized 36-month comparative study of valproic acid (VPA), phenytoin (PHT), phenobarbital (PB) and carbamazepine (CBZ) efficacy in patients with newly diagnosed epilepsy with partial complex seizures," J Neurolog Sci., 150(S1):S162-S163.
Dasa et al., Brhat Nighantu Ratnakara (Saligramanighantubhusanam). vol. IV. 1997:170. Sanskrit. Exhibit 5.
Davis et al., (1949). "Antiepileptic action of marijuana-active substances," Federation Proceedings, 8:284-285.
Davis et al., (2003). "A predominant role for inhibition of the adenylate cyclase/protein kinase A pathway in ERK activation by cannabinoid receptor 1 in NIE-115 neuroblastoma cells," J Biol Chem., 5;278(49):48973-48980.
De Meijer, "Chapter 5: The Chemical Phenotypes (Chemotypes) of Cannabis," Handbook of Cannabis, ed. Roger G. Pertwee, 2014, 89-110.
De Oliveira et al., (2016). "Anticonvulsant activity of beta-caryophyllene against pentylenetetrazol-induced seizures," Epilepsy Behav, 56:26-31.

Decision in Opposition proceedings (Art. 101(3)(a) and 106(2) EPC in European Patent Application No. EP2448637, dated Dec. 15, 2016, 91 pages.
Declaration of Professor Anthony G. Marson In the Inter Partes Review of U.S. Pat. No. 9,066,920, Dated Dec. 13, 2016, 28 pages.
Declaration of Professor Leslie Benet In the Inter Partes Review of U.S. Pat. No. 9,066,920, Dated Nov. 22, 2016, 18 pages.
Deshpande et al., (2007). "Cannabinoid CBI receptor antagonists cause status epilepticus-like activity in the hippocampal neuronal culture model of acquired epilepsy," Neurosci Lett., 411(1):11-16.
Devinsky et al., (2014). "Cannabidiol: Pharmacology and potential therapeutic role in epilepsy and other neuropsychiatric disorders," Epilepsia, 55(6):791-802.
Dravet (2011). "The core Dravet syndrome phenotype," Epilepsia, 52(S2):3-9.
Dreifos et al., (1981). "Proposal for Revised Clinical and Electroencephalographic Classification of Epileptic Seizures," Epilepsia, 22:489-501.
Dulac et al., (1991). "Vigabatrin in Childhood Epilepsy," J. Child Neurolog., 6(S2):S30-S37.
Dulac et al., (1997). "Use of Lamotrigine in Lennox-Gastaut and Related Epilepsy Syndromes," J. Child Neurolog., 12(S1):S23-S29.
Eadie (2014). "Shortcomings in the current treatment of epilepsy," Expert Rev Neurother., 12:1419-27.
Eggers (2007). "Temporal lobe epilepsy is a disease of faulty neuronal resonators rather than oscillators, and all seizures are provoked, usually by stress," Med Hypotheses, 69(6):1284-1289.
ElSohly and Gul, "Chapter 1: Constituents of *Cannabis sativa*," Handbook of Cannabis, 2014, ed. Roger G. Pertwee, 3-22.
Engel (2006). "Report of the ILAE classification core group," Epilepsia, 47(9):1558-1568.
Engel et al., Chapter 1, "What Should be Modeled," In Models Seizure Epilepsy., 2006, 14 pages.
EPO Opposition, Expert Statement of Dr. Emma Louise Cheetham in European Appln. No. EP10734541.5, dated Nov. 4, 2016, 1 pages.
EPO Opposition, Expert Statement of Professor Anthony G Marson in European Appln. No. EP10734541.5, dated Jun. 14, 2016, 9 pages.
EPO Opposition, Expert Statement of Professor Benjamin J. Whalley in European Appln. No. EP10734541.5, dated Sep. 9, 2016, 11 pages.
EPO Opposition, Expert Statement of Vincenzo Di Marzo in European Appln. No. EP10734541.5, dated Sep. 9, 2016, 10 pages.
EPO Opposition, Supplemental Expert Statement of Professor Benjamin J. Whalley, dated Nov. 4, 2016, 9 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
EPO Statement of Grounds of Appeal in European Appln. No. 10734541.5, dated Apr. 12, 2017, 6 pages.
EPO Statement of Grounds of Appeal in European Appln. No. 10734541.5, dated Apr. 21, 2017, 14 pages.
EPO Third Party Observations in European Appln. No. EP10734541.5, dated Apr. 3, 2017, 19 pages.
Examination Report mailed Feb. 29, 2012 for Application No. GBI 121919.3.
Examination Report mailed Mar. 18, 2014 for Application No. GBI 100043.7.
Fariello et al., (1976). "Parenteral Penicillin in Rats: An Experimental Model of Multifocal Epilepsy," Epilepsia, 17(2):217-222.
FDA [online], "Warning Letters and Test Results for Cannabidiol-Related Products," 2015 Warning Letters, retrieved on Nov. 14, 2017, URL <https://www.fda.gov/newsevents/publichealthfocus/ucm484 I 09.htm>, 4 pages.
FDA [online], "Warning Letters and Test Results for Cannabidiol-Related Products," 2016 Warning Letters, retrieved on Nov. 14, 2017, URL <https://www.fda.gov/newsevents/publichealthfocus/ucm484 I09.htm>, 4 pages.
Ferdinand et al., (2005). "Cannabis—psychosis pathway independent of other types of psychopathology," Schizophr Res., 79(2-3):289-295.

(56) References Cited

OTHER PUBLICATIONS

Fisher et al., (2000). "The impact of epilepsy from the patient's perspective I. Descriptions and subjective perceptions," Epilepsy Res., 41(1):39-51.
Gabor et al., (1990). "Lorazepam versus phenobarbital: Candidates for drug of choice for treatment of status epilepticus," J Epilepsy, 3(1):3-6.
Gallily et al., (2015). "Overcoming the Bell-Shaped Dose-Response of Cannabidiol by Usi.ng Cannabis Extract Enriched in Cannabidiol," Pharmacology & Pharmacy, 6(2):75-85.
Gardner [online], "Comes Now Epidiolex (FDA Approves IND Studies of CBD)," BeyondTHC.com, Oct. 22, 2013, retrieved on Jan. 31, 2018, URL <http://www.beyondthc.com/comes-now-epidiolex-fda-approves-ind-studies-of-cbd>, 4 pages.
Gastaut (1970). "Clinical and electroencephalographical classification of epileptic seizures," Epilepsia, 11(1):102-112.
GB Combined Search and Examination Report in Application No. GB1611544.6, dated Mar. 29, 2017, 8 pages.
GB Combined Search and Examination Report in GB Appln. No. GB1514079.1, dated May 4, 2016, 9 pages.
GB Combined Search and Examination Report in GB Appln. No. GB1605448.8, dated Jan. 12, 2017, 6 pages.
GB Combined Search and Examination Report in GB Appln. No. GB1621480.11, dated Sep. 22, 2017, pages.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde presentation.pdf, Sep. 9-11, 2014>, 45 pages.
Gedde, M. et al Epilepsy Currents 2014 Posters excerpt pp. 449-450.
Geffrey et al., "Cannabidiol (CBD) Treatment for Refractory Epilepsy in Tuberous Sclerosis Complex (TSC)," American Epilepsy Society., Annual Meeting Abstracts: View, Abstract 2.427, 2014, retrieved on Feb. 10, 2017, retrieved from the internet: URL <https://www.aesnet.org/meetings events/annual meeting abstracts/view/1868979>, 2 pages.
Green, "CBD: An Unconventional Therapy," available online at http://nugs.com/article/cbd-an- unconventional-therapy.html, published Mar. 24, 2014, 5 pages.
Gresham et al., (2010). "Treating Lennox-Gastaut syndrome in epileptic pediatric patients with third-generation rufinamide," Neuropsychiatr Dis Treat., 6:639-645.
Gross et al., (2004). "Marijuana use and epilepsy: prevalence in patients of a tertiary care epilepsy center," Neurology, 62(11):2095-2097.
Grotenhermen, "Epilepsiebehandlung des Angelman-Syndroms mit CBD (Cannabidiol) (Epilepsy treatment of Angelman syndrome with CBD (cannabidiol)," Angelman e.V., Jan. 2015, retrieved on Jun. 7, 2019, URL <http://s8a85e4d6fcfb04b6.jimcontent.com/download/version/1472724876/module/9873059694/name/Epilepsiebehandlung%20durch%20CBD.pdf>, 8 pages (with Machine translation).
Guerrini et al., (1998). "Lamotrigine and Seizure Aggravation in Severe Myoclonic Epilepsy," Epilepsia, 39(5):508-512.
Guimaraes et al., (1990). "Antianxiety effect of cannabidiol in the elevated plus-maze," Psychopharmacology, 100:558-559.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
Heinemann et al., "An Overview of In Vitro Seizure Models in Acute and Organotypic Slices," Chapter 4, 35-44, 2006.
Hill (2013). "Cannabidivarin-rich cannabis extracts are anticonvulsant in mouse and rat via a CB1 receptor-independent mechanism," British Journal of Pharmacology, 170(3): 679-692.
Hill et al., (2010). "delta-Tetrahydrocannabivarin suppresses in vitro epileptiform and in vivo seizure activity in adult rats," Epilepsia, 51(8):1522-1532.
Hill et al., (2012). "Cannabidivarin is anticonvulsant in mouse and rat," Br J Pharmacol, 167(8):1629-1642.
Holmes et al., (2008). "Choosing the Correct AED: From Animal Studies to the Clinic," Pediatr Neurol, 38(3):151-162.
Iannotti et al., (2014). "Nonpsychotropic plant cannabinoids, cannabidivarin (CBDV) and cannabidiol (CBD), activate and desensitize transient receptor potential vanilloid I (TRPVI) channels in vitro: Potential for the treatment of neuronal hyperexcitability," ACS Chem. Neurosci., 5(11):1131-1141.
ICE Epilepsy Alliance, The Dravet Syndrome Spectrum, Nov. 2008, 2 pages.
INSYS Development Company, Inc. v. GW Pharma Limited and Otsuka Pharmaceutical Co., Ltd., Decision in IPR2017-00503, U.S. Pat. No. 9,066,920, dated Jul. 7, 2017, 26 pages.
INSYS Development Company, Inc. v. GW Pharma Limited and Otsuka Pharmaceutical Co., Ltd., Declaration by Mark Polyakov, IPR2017-00503, U.S. Pat. No. 9,066,920, dated May 29, 2018, 1 page.
INSYS Development Company, Inc. v. GW Pharma Limited and Otsuka Pharmaceutical Co., Ltd., Declaration of Professor H. Steve White in IPR2017-00503, U.S. Pat. No. 9,066,920, dated Oct. 24, 2017, 69 pages.
INSYS Development Company, Inc. v. GW Pharma Limited and Otsuka Pharmaceutical Co., Ltd., Deposition of H. Steve White, dated Dec. 13, 2016, 50 pages.
INSYS Development Company, Inc. v. GW Pharma Limited and Otsuka Pharmaceutical Co., Ltd., Final Written Decision in IPR2017-00503, U.S. Pat. No. 9,066,920, dated Jan. 3, 2019, 40 pages.
INSYS Development Company, Inc. v. GW Pharma Limited and Otsuka Pharmaceutical Co., Ltd., Patent Owners' Preliminary Response in IPR2017-00503, U.S. Pat. No. 9,066,920, dated Apr. 11, 2017, 45 pages.
INSYS Development Company, Inc. v. GW Pharma Limited and Otsuka Pharmaceutical Co., Ltd., Petitioner's Brief Regarding Ground III of the IPR, IPR2017-00503, U.S. Pat. No. 9,066,920, dated May 29, 2018, 45 pages.
INSYS Development Company, Inc. v. GW Pharma Limited and Otsuka Pharmaceutical Co., Ltd., Petitioner's Reply to Patent Owner's Response, IPR2017-00503, U.S. Pat. No. 9,066,920, dated Jun. 19, 2018, 6 pages.
INSYS Development Company, Inc. v. GW Pharma Limited and Otsuka Pharmaceutical Co., Ltd., Petitioner's Reply to Response in IPR2017-00503, U.S. Pat. No. 9,066,920, dated Jan. 19, 2018, 36 pages.
International Preliminary Report on Patentability in International Application No. PCT/GB2010/051066, dated May 3, 2011, 6 pages.
International Preliminary Report on Patentability mailed Apr. 18, 2017 for Application No. PCT/GB2015/053030, 6 pages.
International Preliminary Report on Patentability mailed Dec. 12, 2013 for Application No. PCT/GB2012/052284, 12 pages.
International Preliminary Report on Patentability mailed Jun. 9, 2011 for Application No. PCT/GB2010/051066, 6 pages.
International Search Report and Written Opinion mailed Dec. 13, 2010 for Application No. PCT/GB2010/051066.
International Search Report and Written Opinion mailed May 30, 2011 for Application No. PCT/GB2011/050649, 15 pages.
International Search Report and Written Opinion mailed Nov. 16, 2012 for Application No. PCT/GB2012/052284.
International Search Report in International Application No. PCT/GB20 I 0/051066, dated Nov. 16, 2010, 3 Pages.
International Search Report mailed Feb. 24, 2012 for Application No. PCT/GB2012/050002, 3 pages.
IUPHAR/BPS Guide to Pharmacology [online], "Entry for ./19-tetrahydrocannabidiol," available on or before Mar. 29, 2016, retrieved on Jun. 20, 2018, URL <http://www.guidetopharmacology.org/GRAC/LigandDisplayForward?tab=biology&ligandid=242>, 2 pages.
Iuvone et al., (2004). "Neuroprotective effect of cannabidiol, a non-psychoactive component from *Cannabis sativa*, on beta-amyloid-induced toxicity in PC12 cells," J Neurochem., 89(1):134-141.
Jacobson et al. "Survey of Current Cannabidiol Use in Pediatric Treatment-Resistant Epilepsy," Apr. 22, 2013, XP055238831, Retrieved

(56) References Cited

OTHER PUBLICATIONS from the Internet, <https://www.thcint.com/uploads/1/9/3/7/1937 I 199/cannabidiol use in pediatric epilepsy.pdf>.
Jeavons et al., (1974). "Sodium valproate in treatment of epilepsy," Br Med J. 1974, 2(5919):584-586.
Jones et al. [online], Info & Metrics/ Article Information," Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Jones et al., Cannabidiol displays antiepileptiform and antiseizure properties in vitro and in vivo. J Pharmacol Exp Ther. Feb. 2010;332(2):569-77. doi: 10.1124/jpet.109.159145. Epub Nov. 11, 2009.
Joy et al., Marijuana and Medicine. Assessing the Science Base. National Academy Press. Washington D.C. 1999. 170 pages.
Kahan et al., (2015). "Risk of Selection Bias in Randomized Trials," Trials, 16:405, 7 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al., (1973). "The anticonvulsant activity of cannabidiol and cannabinol," Life Science, 13(11):1527-1531.
Karler et al., (1981). "The cannabinoids as potential antiepileptics," J Clin Pharmacol., 21(S1):437S-447S.
Khan et al., Khazaain-al-Adiva. vol. I. 1911:885. Urdu. Exhibit 7.
Khan et al., Khazaain-al-Adiva. vol. I. 1911:886. Urdu. Exhibit 4.
Khan et al., Khazaain-al-Advia, vol. I. 1911: 889. Urdu. Exhibit 3.
Khan et al., Khazaain-al-Advia, vol. I. 1911: 889. Urdu. Exhibit 4.
Khan et al., Muheet-e-Azam, vol. II. 1887: 147. Persian. Exhibit 1.
Klitgaard et al., (1998). "Evidence for a unique profile of levetiracetam in rodent models of seizures and epilepsy," European J Pharm, 353(2):191-206.
Klitgaard et al., (2003). "Electrophysiological, neurochemical and regional effects of levetiracetam in the rat pilocarpine model of temporal lobe epilepsy," Seizure, 12(2):92-100.
Kramer et al., (2011). "Febrile infection-related epilepsy syndrome (FIRES): pathogenesis, treatment, and outcome: a multicenter study on 77 children," Epilepsia, 52(11):1956-1965.
Kruk-Slomka et al., (2014). "A comparison of mecamylamine and bupropion effects on memory-related responses induced by nicotine and scopolamine in the novel object recognition test in mice," Pharmacological Reports, 66(4):638-646.
Kuhn et al., (2007). "Potent activity of carfilzomib, a novel, irreversible inhibitor of the ubiquitin-proteasome pathway, against preclinical models of multiple myeloma," Blood, Nov. 2007, 110(9): 3281-3290.
Kurz et al., (2010). "Use of dronabinol (delta-9-THC) in autism: a prospective single-case-study with an early infantile autistic child," Cannabinoids, 5(4):4-6.
Kwan et al., (2010). "Definition of drug resistant epilepsy: consensus proposal by the ad hoc Task Force of the ILAE Commission on Therapeutic Strategies," Epilepsia, 51(6):1069-1077.
LaPrairie et al., (2015). "Cannabidiol is a negative allosteric modulator of the cannabinoid CB1 receptor," British J Pharmacology, 172(20):4790-4805.
Leo et al., (2016). "Cannabidiol and epilepsy: Rationale and therapeutic potential," Pharmacological Research, 107:85-92.
Letter from Opponent Regarding Oral Proceedings in European Patent No. EP2448637, dated Oct. 20, 2016, 6 pages.
Lewis, "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.
Lieu et al., (2010). "Assessment of self-selection bias in a pediatric unilateral hearing loss study," Otolaryngol Head Neck Surg., 142(3):427-433.
Lindamood et al., (1980). "Effects of A9-Tetrahydrocannabinol and Cannabidiol on Sodium-Dependent High Affinity Choline Uptake in the Rat Hippocampus," J Pharmacology Experimental Therapeutics, 213(2):216-221.
Long et al., (2005). "The pharmacological actions of cannabidiol," Drugs of the Future, 30(7):747-753.
Loscher et al., (2011). "Modem antiepileptic drug development has failed to deliver: ways out of the current dilemma," Epilepsia, 52(4):657-678.
Lowenstein D.H., Chapter 363, Section 2 "Diseases of the Central Nervous System," Seizures and Epilepsy, 2498-2512, 2008.
Luttjohann et al., (2009). "A Revised Racine's scale for PTZ-induced seizures in rats," Physiology & Behavior, 98(5):579-586.
Lutz (2004). "On-demand activation of the endocannabinoid system in the control of neuronal excitability and epileptiform seizures," Biochem Pharmacol., 68(9):1691-1698.
Izzo et al., (2009). "Non-psychotropic plant cannabinoids: new therapeutic opportunities from an ancient herb," Trends in Pharmacological Sciences, 30(10):515-527.
Maa et al., (2014). "The case for medical marijuana in epilepsy," Epilepsia, 55(6):783-786.
Mackie (2006). "Cannabinoid receptors as therapeutic targets," Annu Rev Pharmacol Toxicol., 46:101-122.
Majoosi, et al. Kaamil-al-Sena'ah, Part II, Central Council for Research in Unani Medicine. 2005:116. Arabic. Exhibit 2.
Malfait et al., (2000). "The nonpsychoactive cannabis constituent cannabidiol is an oral anti-arthritic therapeutic in murine collagen-induced arthritis," PNAS, 97(17):9561-9566.
Manno (2011). "Status Epilepticus: Current Treatment Strategies," The Neurohospitalist, 1(1):23-31.
Mares et al., "Chapter 12: Electrical Stimulation-Induced Models of Seizures," Model of Seizures and Epilepsy, Asla Pitkanen, Philip A. Schwartzkroin & Solomon L. Moshe, eds., 2004, 153-159.
Martin et al., (1987). "Structure-Anticonvulsant Activity Relationships of Cannabidiol Analogs," National Institute on Drug Abuse, Research Monograph Series, 79:48-58.
Mattson et al., (1985). "Comparison of carbamazepine, phenobarbital, phenytoin, and primidone in partial and secondarily generalized tonic-clonic seizures," New England Journal of Medicine, 313:145-151.
Mattson et al., (1996). "Prognosis for total control of complex partial and secondary generalized tonic clonic seizures," Neurology, 47(1):68-76.
Mccormick et al., (2001). "On the cellular and network bases of epileptic seizures," Annu Rev Physiol., 63:815-846.
McNamara, "Chapter 19: Pharmacotherapy of the Epilepsies,", Goodman & Gilman's The Pharmacological Basis of Therapeutics 11th ed., McGraw-Hill Companies, 2006, 501-525.
Mechoulam et al., (1978). "Toward drugs derived from cannabis," Naturwissenschaften, 65(4):174-179.
Mechoulam et al., (2002). "Cannabidiol: An Overview of Some Pharmacological Aspects," J Clin Pharmacol., 42(S1):11S-19S.
Merlis (1970). "Proposal for an international classification of the epilepsies," Epilepsia, 11(1):114-119.
Miller et al., (2013). "Mapping genetic modifiers of survival in a mouse model of Dravet syndrome," Genes, Brain and Behavior, 13(2):163-172.
Moral et al., (2014). "Pipeline on the move," Drugs of the Future, 39(1): 49-56.
Morard et al., (2007). "Conversion to Sirolimus-Based Immunosuppression in Maintenance Liver Transplantation Patients," Liver Transplantation, 13:658-664.
Morelli et al., (2014). "The effects of cannabidiol and its synergism with bortezomib in multiple myeloma cell lines. A role for transient receptor potential Vanilloid type-2," Int J Cancer, 134(11): 2534-2546.
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Nabissi et al., (2016). "Cannabinoids synergize with cafilzomib, reducing multiple myeloma cells viability and migration," Oncotarget, 7(47):77543-77557.

(56) References Cited

OTHER PUBLICATIONS

Neto et al., (2009). "The role of polar phytocomplexes on anticonvulsant effects of leaf extracts of Lippia alba (Mill.) N.E. Brown chemotypes," J. Pharm Pharmacol., 61(7):933-939.
Ng et al., (1990). "Illicit drug use and the risk of new-onset seizures," Am J Epidemiol., 132(1):47-57.
Notice of Allowance in U.S. Appl. No. 13/380,305, mailed Dec. 10, 2014, 5 pages.
Notice of Allowance in U.S. Appl. No. 13/380,305, mailed Mar. 19, 2015, 7 pages.
Notice of Appeal in European Patent No. EP2448637, dated Feb. 14, 2017, 5 pages.
Notice of Opposition to a European Patent No. EP2448637, Dated Dec. 5, 2014, 20 pages.
Oakley et al., (2011). "Dravet Syndrome Insights into pathophysiology and therapy from a mouse model of Dravet syndrome," Epilepsia, 52(S2):59-61.
Obay et al., (2007). "Antiepileptic effects of ghrelin on pentylenetetrazole-induced seizures in rats," Peptides, 28(6):1214-1219.
Office Action in U.S. Appl. No. 13/380,305, dated Aug. 25, 2014.
Opponent Response to the Preliminary Opinion of the Opposition Division in European Patent No. EP2448637, dated Jun. 23, 2016, 27 pages.
Opponent Response to the Preliminary Opinion of the Opposition Division in European Patent No. EP2448637, dated Sep. 9, 2016, 25 pages.
Opponent Response to the Written Submissions in European Patent No. EP2448637, dated Oct. 12, 2016, 18 pages.
Opponent Response to the Written Submissions in European Patent No. EP2448637, dated Oct. 20, 2016, 3pages.
Opponent Written Submission in European Patent No. EP2448637, dated Nov. 4, 2016, 3 pages.
PCT International Preliminary Report on Patentability in International Appln. No. PCT/GB2015/051775, dated Aug. 10, 2016, 9 pages.
PCT International Preliminary Report on Patentability in International Appln. No. PCT/GB2016/051792, dated Sep. 1, 2017, 14 pages.
PCT International Preliminary Report on Patentability in International Appln. No. PCT/GB2017/052229, dated Feb. 26, 2019, 7 pages.
PCT International Preliminary Report on Patentability in International Appln. No. PCT/US2017/050868, dated Oct. 11, 2018, 7 pages.
PCT International Search Report and Written Opinion in International Appln. No. PCT/GB2015/051775, dated Aug. 26, 2015, 11 pages.
PCT International Search Report and Written Opinion in International Appln. No. PCT/GB2015/051776, dated Aug. 25, 2015, 11 pages.
PCT International Search Report and Written Opinion in International Appln. No. PCT/GB2017/051913, dated Sep. 15, 2017, 9 pages.
PCT International Search Report and Written Opinion in International Appln. No. PCT/GB2017/051914, dated Sep. 12, 2017, 10 pages.
PCT International Search Report and Written Opinion in International Appln. No. PCT/GB2017/052229, dated Oct. 6, 2017, 10 pages.
PCT International Search Report and Written Opinion in International Appln. No. PCT/GB2017/053735, dated Mar. 14, 2018, 14 pages.
PCT International Search Report and Written Opinion in International Appln. No. PCT/US2017/050868, dated Aug. 6, 2017, 14 pages.
PCT International Search Report and Written Opinion in International Appln. PCT/GB2017/051943, dated Sep. 12, 2017, 10 pages.
Pelliccia et al., "Treatment with CBD in oily solution of drug-resistant paediatric epilepsies," Available online Sep. 2, 2010, Retrieved Jun. 30, 2015, Retrieved from the internet: URL http://www.cannabis-med.org/studies/ww_en_db_study_show.php?s_id=173&&search_pattern=EPILEPSY, 2 pages, Abstract only.
Pereira et al., (2007). "Study pharmacologic of the GABAergic and glutamatergic drugs on seizures and status epilepticus induced by pilocarpine in adult Wistar rats," Neurosci Lett., 419(3):253-257.
Pertwee (2000). "Cannabinoid receptor ligands: clinical and neuropharmacological considerations, relevant to future drug discovery and development." Expert Opin Investig Drugs., 9(7):1553-1571.
Pertwee (2008). "The diverse CB1 and CB2 receptor pharmacology of three plant cannabinoids: Δ9-tetrahydrocannabinol, cannabidiol and Δ9-tetrahydrocarmabivarin," Br. J. Pharmacol., 153(2):199-215.
Pertwee, Chapter 3, "The Pharmacology and Therapeutic Potential of Cannabidiol," pp. 32-83 in the book Neuroscience Intelligence Unit: Cannabinoids, Ed Vincenzo Di Marzo, Springer Science & Business Media, (2004).
Petition for Inter Partes Review of U.S. Pat. No. 9,066,920, dated Dec. 16, 2016, 77 pages.
Petrocellis et al., (2011). "Effects of cannabinoids and cannabinoid-enriched Cannabis extracts on TRP channels and endocannabinoid metabolic enzymes," British Journal of Pharmacology, 163(7):1479-1494.
Physician's Desk Reference, 63rd Ed., 2009, 423-431, 2192-2194, 2639-2242, 3019-3022.
Pohl et al., (1987). "Effects of flunarizine on Metrazol-induced seizures in developing rats," Epilepsy Res., 1(5):302-305.
Poortman-van der Meer (1999). "A contribution to the improvement of accuracy in the quantitation of THC," Forensic Science International, 101(1):1-8.
Porter et al., (2007). "Randomized, multicenter, dose-ranging trial of retigabine for partial-onset seizures," Neurology, 68(15):1197-1204.
Porter et al., (2013). "Report of a parent survey of cannabidiol-enriched cannabis use in pediatric treatment-resistant epilepsy," Epilepsy Behav., 29(3):574-577.
Potter, "Chapter 4: Cannabis Horticulture," Handbook of Cannabis, ed. Roger G. Pertwee, 2014, 65-88.
Pouton (2000). "Lipid formulations for oral administration of drugs: non-emulsifying, self-emulsifying and 'self-microemulsifying' drug delivery systems," Eur. J Pharm Sci., 11(S2):S93-S98.
Press et al., (2015). "Parental reporting of response to oral cannabis extracts for treatment of refractory epilepsy," Epilepsy Behav., 45:49-52.
Pruitt et al., (1984). "Ethanol in Liquid Preparations Intended for Children," Pediatrics, 73(3):405-407.
Raab et al., (2009). "Multiple myeloma," Lancet, 374(9686):324-339.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoidhelp-you/>, 4 pages.
Ramantani et al., (2014). "Epilepsy in Aicardi—Goutieres syndrome," Official J Eur Paediatric Neurology Society, 18(1):30-37.
Rauca et al., (2004). "The role of superoxide dismutase and alpha-tocopherol in the development of seizures and kindling induced by pentylenetetrazol—influence of the radical scavenger alpha-phenyl-N-tert-butyl nitrone," Brain Res., 1009(1-2):203-212.
Reply of the Patent Proprietor to the Notice(s) of Opposition in European Patent No. 2448637, dated May 28, 2015, 12 pages.
Reply to Communication from the Examining Division in European Patent Application No. 1073454 I.5, dated Feb. 15, 2013, 54 pages.
Reply to EPO Communication in European Patent No. EP2448637, dated Nov. 2, 2016, 45 pages.
Reply to Opponent's Written Submission in European Patent No. EP2448637, dated Nov. 4, 2016 13 pages.
Reply to Opponent's Written Submissions in European Patent No. EP2448637, dated Oct. 18, 2016, 5 pages.
Reply to Preliminary Opinion and Opponent's Observations in European Patent No. EP2448637, dated Sep. 9, 2016, 65 pages.

(56) References Cited

OTHER PUBLICATIONS

Request for Continued Examination with the Amendment and Information Disclosure Statement in U.S. Appl. No. 13/380,305, filed Mar. 2, 2015, 3 pages.
Resstel et al., (2009). "5-HT1A receptors are involved in the cannabidiol-induced attenuation of behavioural and cardiovascular responses to acute restraint stress in rats," Br J Pharmacol., 156(1):181-188.
Rosenberg et al., (2015). "Cannabinoids and Epilepsy," Neurotherapeutics, 12(4):747-768.
Rosenkrantz et al., (1972). "Oral and Parenteral Formulations of Marijuana Constituents," J Pharm Sci., 61(7):1106-1112.
Rubio et al., (2010). "In Vivo Experimental Models of Epilepsy," Central Nervous System Agents in Medicinal Chemistry, 10(4):298-309.
Russo (2011). "Taming THC: potential cannabis synergy and phytocannabinoid-terpenoid entourage effects," British J. of Pharm., 163(7):1344-1364.
Sadanandasarma et al., Rasatarangini. 11th Ed. 1979:720-3. Sanskrit. Exhibit 6.
Sander (2003). "The epidemiology of epilepsy revisited," Curr Opin Neurol., 16(2):165-170.
Sandyk et al., "Preliminary trial of cannabidiol in Huntington's Disease," Marihuana: An International Research Report, 1988, 157-162.
Sastri et al., Anandakandam. 1st Edition. 1952:241. Sanskrit. Exhibit 2.
Scuderi et al., (2009). "Cannabidiol in medicine: a review of its therapeutic potential in CNS disorders," Phytother Res., 23(5):597-602.
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., (2006). "Clobazam as Add-on Therapy in Children with Epileptic Encephalopathy," Can J Neurol Sci., 33(2):209-213.
Sperling et al., (2010). "Carisbamate as adjunctive treatment of partial onset seizures in adults in two randomized, placebo-controlled trials," Epilepsia, 51(3):333-343.
Stafstrom et al., (2006). "Models of Pediatric Epilepsies: Strategies and Opportunities," Epilepsia, 47(8):1407-1414.
Statement of Opposition for EP10734541.5 mailed Dec. 5, 2014.
Stephenson (2016). "In Memoriam: Professor Jean Aicardi (1926-2015)," Pediatric Neurology, 54:3-4.
Stott et al., (2004). "Cannabinoids for the pharmaceutical industry." Euphytica, 140:83-93.
Strickley, "Solubilizing Excipients in Oral and Injectable Formulations," Table VIII, Pharmaceutical Research, Feb. 2004, 21(2):201-230.
Swann et al., (2004). "The effects of seizures on the connectivity and circuitry of the developing brain," Ment Retard Dev Disabil Res Rev., 10(2):96-100.
Third Party Observations for Application No. AU2012314128 mailed Mar. 19, 2015.
Third Party Observations for Application No. EPI 1712658.1 mailed Nov. 22, 2013.
Third Preliminary Amendment under 37 C.F.R. 1.115 in U.S. Appl. No. 13/380,305, dated May 23, 2014, 4 pages.
Thomas et al., (2005). "Evidence that the plant cannabinoid Delta9-tetrahydrocannabivarin is a cannabinoid CB1 and CB2 receptor antagonist," Br J Pharmacol., 146(7):917-926.
Thomas et al., (2007). "Cannabidiol displays unexpectedly high potency as an antagonist of CB1 and CB2 receptor agonists in vitro," British J Pharmacology, 150(5):613-623.
Thumma et al., (2008). "Influence of plasticizers on the stability and release of a prodrug of Δ9-tetrahydrocannabinol incorporated in poly (ethylene oxide) matrices," Eur J Pharmaceutics and Biopharmaceutics, 70(2):605-614.
Thurman et al., (2011). "Standards for epidemiologic studies and surveillance of epilepsy," Epilepsia, 52(S7):2-26.
Thurstone, "Avoid Charlotte's Web for Epilepsy," Jun. 26, 2014, URL <http://drthurstone.com/charlotted-web-not-safest-option-epilepsy-treatment/>, 4 pages.
Trembly et al., "Double-blind clinical study of cannabidiol as a secondary anticonvulsant." Marijuana '90 International Conference on Cannabis and Cannabinoids. Kolymbari, Crete. Jul. 8-11. 1990.
Turkanis et al., (1979). "An Electrophysiological Analysis of the Anticonvulsant Action of Cannabidiol on Limbic Seizures in Conscious Rats," Epilepsia, 20(4):351-363.
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Unimed Pharmaceuticals, Inc., "Marinol®," Jul. 2006 <https://www.accessdata.fda.gov/dmgsatfda docs/label/2006/018651s025s026lbl.pdf>, 11 pages.
Usami et al., (1999). "Synthesis and pharmacological evaluation in mice of halogenated cannabidiol derivatives," Chem Pharm Bull (Tokyo)., 47(11):1641-1645.
USPTO Information Disclosure StatementFormPTO-1449 in U.S. Appl. No. 13/380,305, dated Nov. 24, 2014, 8 pages.
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel (2008). "Treatment of Lennox-Gastaut Syndrome: overview and recent findings," Neuropsychiatr Dis Treat., 4(6):1001-1019.
Velasco et al., (2016). "Anticancer mechanisms of cannabinoids," Curr Oncol., 23(S1):S23-S32.
Velisek., "Models of Chemically-Induced Acute Seizures," Models Seizure Epilepsy., 127-152, 2006.
Veliskova, Chapter 48 "Behavioral Characterization of Seizures in Rates," Models Seizures Epilepsy, 601-611, 2006.
Vollner et al., (1969). "Haschisch XX: Cannabidivarin, ein neuer Haschisch-Inhaltsstoff," Tetrahedron Lett., 10(3):145-147.
Wahle et al., (1990). "Development of tolerance to the anticonvulsant effect of valproate but not to ethosuximide in a rat model of absence epilepsy," Eur J Pharma., 181(1-2):1-8.
Wallace et al., (2001). "Assessment of the role of CB1 receptors in cannabinoid anticonvulsant effects," Eur J Pharmacol., 428(1):51-57.
Wallace et al., (2016). "Pharmacotherapy for Dravet syndrome," Pediatr. Drugs, 18:197-208.
Weston et al., "Tetrahydrocannabivarin exhibits anticonvulsant effects in a piriform cortical brain slice model of epileptiform activity." Pro British Pharm Soc 75th Anniv Meeting. Dec. 31, 2006 Found on: http://www.pA2online.org/abstract/abstract.jsp?abid=28533. Abstract Only. 1 Page.
Wingerchuk (2004). "Cannabis for medical purposes: cultivating science, weeding out the fiction." Lancet, 364(9431):315-316.
Written Opinion of the International Application No. PCT/GB2010/051066, dated Nov. 22, 2010, 4 pages.
Yu et al., (2006). "Reduced sodium current in GABAergic interneurons in a mouse model of severe myoclonic epilepsy in infancy," Nature Neuroscience, 9(9): 1142-1149.
Yuriev, "Endogenic cannabinoid system is a new perspective object of pharmacotherapeutic effect to disease of nervous system", Ukrainsky Metodichny Chasopis, 2005; 6(50): 21-9.
Zamberletti et al., (2014). "Alterations of prefrontal cortex GABAergic transmission in the complex psychotic-like phenotype induced by adolescent delta-9-tetrahydrocannabinol exposure in rats," Neurobiology of Disease, 63:35-47.
Zhao et al., Chapter 27 "Repetitive Seizures in the Immature Brain," Models Seizures Epilepsy., 341-350, 2006.
Zhornitsky et al., (2012). "Cannabidiol in Humans—The Quest for Therapeutic Targets," Pharmaceuticals, 5(5):529-552.
Zuardi et al., (2006). "Cannabidiol, a *Cannabis sativa* constituent, as an antipsychotic drug," Braz J Med Biol Res., 39(4):421-429.
Zuardi et al., (2008). "Cannabidiol: from an inactive cannabinoid to a drug with wide spectrum of action," Rev Bras Psiquiatr., 30(3): 271-280.

(56) References Cited

OTHER PUBLICATIONS

Charlotte's Web. "When to Expect Results from CW Hemp Oil," Mar. 13, 2017, retrieved on May 21, 2018, <https://www.cwhemp.com/blog/expecting-results-from-hemp>, 6 pages.
AU Examination Report for Application No. 2012204800, dated Oct. 22, 2019, 4 pages.
Combined Search and Exam Report dated Apr. 24, 2017 for GB Application No. GB1614522.9, 4 pages.
Combined Search and Exam Report dated Dec. 8, 2017 for GB Application No. GB1703115.4 5 pages.
Combined Search and Exam Report dated Jul. 6, 2021 for GB Application No. GB2102010.2, 4 pages.
Combined Search and Examination Report mailed Feb. 27, 2015 for GB Application No. GB1410771.8, 7 pages.
Combined Search and Examination Report mailed Feb. 25, 2016 for GB Application No. GB1510664.4, 6 pages.
Declaration of Sean D. McAllister and Pierre-Yves Desprez dated Nov. 26, 2012, filed in U.S. Appl. No. 12/600,553, 19 pages.
EPO Auxiliary Requests to the File in European Patent No. EP2448637, dated Nov. 2, 2016, 45 pages.
EPO Communication Pursuant to Article 94(3) EPC in European Appln. No. 10734541.5, dated Oct. 23, 2012, 3 pages.
EPO Letter from Opponent Regarding Oral Proceedings in European Patent No. EP2448637, dated Oct. 20, 2016, 6 pages.
EPO Opposition, Expert Statement of Dr. Emma Louise Cheetham in European Appln. No. EP10734541.5, dated Nov. 4, 2016, 6 pages.
Patentee's Response and Amended Claim Set for EP09757810.8, dated Sep. 27, 2013, 9 pages.
PCT International Search Report and Written Opinion mailed Apr. 20, 2018 for International Application No. PCT/GB2018/050421, 12 pages.
PCT International Search Report and Written Opinion mailed Oct. 6, 2017 for International Application No. PCT/GB2017/052229, 10 pages.
PCT International Search Report and Written Opinion mailed Feb. 5, 2016 in International Application No. PCT/GB2015/053028, 13 pages.
PCT International Search Report and Written Opinion mailed May 2, 2022 for International Application No. PCT/GB2022/050221, 8 pages.
PCT International Search Report and Written Opinion mailed Aug. 31, 2016 in International Application No. PCT/GB/2016/051792, 13 pages.
PCT International Search Report and Written Opinion in International Application No. PCT/GB2015/053024, dated Feb. 2, 2016, 9 pages.
PCT International Search Report and Written Opinion in International Appln. No. PCT/GB2016/052340, dated Oct. 25, 2016, 9 pages.
PCT International Preliminary Report on Patentability mailed Oct. 4, 2006 for PCT Application No. PCT/GB2005/003793, filed on Sep. 30, 2005, 6 pages.
PCT International Preliminary Report on Patentability mailed Sep. 18, 2012 for PCT Application No. PCT/GB2011/050478, 6 pages.
PCT International Search Report and Written Opinion mailed Jan. 16, 2006 for PCT Application No. PCT/GB2005/003793, 10 pages.
PCT International Search Report and Written Opinion mailed Aug. 2, 2011 for PCT Application No. PCT/GB2011/050487, 22 pages.
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006258), dated Jun. 21, 2017, 6 pages.
Vietnam Office Action in Application No. 1201400886, dated Sep. 24, 2019, 2 pages, w/English translation.
[Author Unknown], Drug Development & Delivery (2018). "GW Pharmaceuticals Achieves Positive Results in Phase II Study," available online at <https://drug-dev.com/gw-pharmaceuticals-achieves-positive-results-in-phase-ii-study/, 4 pages.
[Author Unknown], Cover and Table of Contents, J Pharmacology and Exp. Therapeutics, Feb. 2020, 332(2), 4 pages.
[Author Unknown] Salutaris Drops Buy Salutaris Drops—Salutaris Drops. Oct. 12, 2014. Last accessed on Jan. 20, 2017 at http:/web.archive.org/web/20141012130255/http://salutarisdrops.com/buy-salutaris-drops, 2 pages.
[Author Unknown] Salutaris Drops Cannabidiol for Aicardi Syndrome—Salutaris Drops, Oct. 12, 2014. Last accessed from http:/web.archive.org/web/20141012220050/http://salutarisdrops.com/cannabidiol-aicardi-syndrome/ on Apr. 20, 2021, 3 pages.
[Author Unknown] Database WPI Week 201252. Clarivate Analytics, Accession No. 2012-J67237, Jan. 8, 2011, 2 pages.
[Author Unknown] GWPharm [online], "GW Pharmaceuticals Announces Preliminary Results of Phase 2a Study for its Pipeline Compound GWP42006," GW Pharmaceuticals Press Release, Feb. 21, 2018, https://www.globenewswire.com/news-release/2018/02/21/1372900/0/en/GW-Pharmaceuticals-Announces-Preliminary-Results-of-Phase-2a-Study-for-its-Pipeline-Compound-GWP42006.html, 5 pages.
[Author Unknown] American Association of Neurological Surgeons (AANS), "Glioblastoma Multiforme," Mar. 2015, last updated Mar. 2015; https://www.aans.org/, 5 pages.
Adalpe et al., "Models of malignant glioma," Drug Discovery Today: Disease Models, 3(2):191-196 (2006).
Arrieta et al., "Protamine inhibits angiogenesis and growth of C6 rat glioma; a synergistic effect when combined with carmustine," EP J. of Cancer, 34(13):2101-2106 (1998).
Ben-Shabat, et al., "New cannabidiol derivatives: synthesis, binding to cannabinoid receptor, and evaluation of their ant-inflammatory activity," J Med Chem., 49(3):1113-1117 (2006).
Berk et al., "Investigating owner use of dietary supplements in dogs with idiopathic epilepsy," Res Vet Sci, 119:276-284 (2018). doi: 10.1016/j.rvsc.2018.07.004. Epub Jul. 24, 2018.
Berrocal, et al., "Temozolamide in previously treated high-grade gliomas patients," J. of Cancer, 37: S343 (2001). Poster 1275, presented on Oct. 24, 2001, 1 page.
Bialer et al., "Progress report on new antiepileptic drugs: a summary of the fourth Eilat conference (Eilat IV)," Epilepsy Research, 111:85-141 (2015).
Blazquez, et al., "Inhibition of tumor angiogenesis by cannabinoids," FASEB J, 17:529-531 (2003).
Blow, "Cell migration: our protruding knowledge," Nature Methods., 4(7):589-594 (2007).
Boiardi, et al., "Efficacy of '8-drugs-in-one-day' combination in treatment of recurrent GBM patients," Journal of Neuro-Oncology, 12:153-158 (1992).
Boyden, "The chemotactic effect of mixtures of antibody and antigen on polymorphonuclear leucocytes," J Exp Med, 115:453-456 (1962).
Brodie et al., "Combining antiepileptic drugs—rational polytherapy," Seizure, 20:369-375 (2011).
Casanova et al., "Inhibition of skin tumor growth and angiogenesis in vivo by activation of cannabinoid receptors," J. Clinical Investigation, 111(1):43-50 (2003).
Chang et al., "Signal transduction mediated by the Ras/Raf/MEK/ERK pathway from cytokine receptors to transcription factors: potential targeting for therapeutic intervention," Leukemia, 7(7):1263-1293 (2003).
Charlotte's Web [online]. "Whole-Plant Cannabinoids Outperform Single Molecule Compounds," CWHemp.com, Jan. 11, 2017, retrieved on Jun. 16, 2017, <https://www.cwhemp.com/blog/whole-plant-cw-hemp-cannabinoids>, 5 pages.
ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, <http://www.childneurologyfoundation.org/disorders/lgs-lennox-gastaut-syndrome, 10 pages.
Chou & Talalay, "Analysis of combined drug effects: a new look at a very old problem," TIPS, 4:450-454 (1983).
Dasa et al., "Key Attributes of TKDL: Ganja," Bhrhat Nighantu Ratnakara (Saligramanighantubhusanam), 1997, with English translation, 5 pages.

(56) References Cited

OTHER PUBLICATIONS

De La Ossa et al., "Local delivery of cannabinoid-loaded microparticles inhibits tumor growth in a murine xenograft model of glioblastoma multiforme," PLoS One, 8(1):e54795 (2013); doi: 10.1371/journal.pone.0054795. Epub Jan. 22, 2013, 8 pages.
De Meijer et al., "The inheritance of chemical phenotype in *Cannabis sativa* L. (II): Cannabigerol predominant plants," Euphytica, 145(1):189-198 (2007).
De Petrocellis et al., "Regulation of transient receptor potential channels of melastatin type 8 (TRPM8): Effect of cAMP, cannabinoid CB1 receptors and endovanilloids," Exp Cell Res., 313(9):1911-1920 (2007). Epub Jan. 18, 2007.
Dulac et al., "Vigabatrin in Childhood Epilepsy," J. Child Neurolog., 6(S2):S30-S37 (1991).
Eadie, "Shortcomings in the current treatment of epilepsy," Expert Rev Neurother., 12(12):1419-1427 (2012).
EPIDIOLEX® (cannabidiol) oral solution, CV, Prescribing Information, 2018, 30 pages; https://www.accessdata.fda.gov/drugsatfda_docs/label/2018/210365lbl.pdf.
FDA [Online], "Warning Letters and Test Results for Cannabidiol-Related Products," 2016 Warning Letters, retrieved on Nov. 14, 2017, URL <https://www.fda.gov/newsevents/publichealthfocus/ucm484109.htm, 4 pages.
Fernandes et al., "Modification of delta9-THC-actions by cannabinol and cannabidiol in the rat," Psychopharmacologia, 38(4):329-338 (1974); doi: 10.1007/BF00429130.
Friedman et al., "Temozolomide and treatment of malignant glioma," Clin Cancer Res., 6(7):2585-2597 (2000).
Gallily et al., "Gamma-irradiation enhances apoptosis induced by cannabidiol, a non-psychotropic cannabinoid, in cultured HL-60 myeloblastic leukemia cells," Leuk Lymphoma, 44(10):1767-1773 (2003).
Galve-Roperh et al., "Anti-tumoral action of cannabinoids: involvement of sustained ceramide accumulation and extracellular signal-regulated kinase activation," Nature Medicine, 6(3):313-319 (2000).
Gaston et al., "Interactions between cannabidiol and commonly used antiepileptic drugs," Epilepsia, 58(9):1586-1592 (2017).
Gilbert, et al., "A phase II study of temozolomide in patients with newly diagnosed supratentorial malignant glioma before radiation therapy," Neuro-Oncology, 4(4):261-267 (2002).
Gloss, "Cannabinoids for epilepsy (Review)," Cochrane Database of Systematic Reviews, 2014, 3, Art No. CD009270, 25 pages.
Grotenhermen, "Pharmacokinetics and Pharmacodynamics of Cannabinoids," Clin. Pharmacokinet., 42(4):327-360 (2003).
Guzman et al., "Control of the cell survival/death decision by cannabinoids," J. Mol Med (Berl)., 78(11):613-625 (2001).
Guzman et al., "Cannabinoids: potential anticancer agents," Nat Rev Cancer, 3(10):745-755 (2003).
Hayakawa et al., "Cannabidiol potentiates pharmacological effects of Delta(9)-tetrahydrocannabinol via CB(1) receptor-dependent mechanism," Brain Res., 1188:157-164 (2003).
Heske et al., "A cohort study of epilepsy among 665,000 insured dogs: Incidence, mortality and survival after diagnosis," The Veterinary Journal, 471-6 (2014); doi:10.1016/j.tvjl.2014.09.023, 6 pages.
Huang et al., "ECRG2 inhibits cancer cell migration, invasion and metastasis through the down-regulation of uPA/plasmin activity," Carcinogenesis, 28(11):2274-2281 (2007); doi:10.1093/carcin/bgm140/.
Huizenga et al., "Preclinical safety and efficacy of cannabidivarin for early life seizures," Neuropharmacology, 148:189-198 (2019).
Hulkower & Herber, "Cell Migration and Invasion Assays as Tools for Drug Discovery," Pharmaceutics, 3:107-124 (2011).
Izzo et al., "Increased endocannabinoid levels reduce the development of precancerous lesions in the mouse colon," J. Mol Med (Berl.), 86(1):89-98 (2008).
Jacobsson et al., "Serum-dependent effects of tamoxifen and cannabinoids upon C6 glioma cell viability," Biochem Pharmacol, 60(12):1807-1813 (2000).

Jacobsson et al., "Inhibition of rat C6 glioma cell proliferation by endogenous and synthetic cannabinoids. Relative involvement of cannabinoid and vanilloid receptors," J. Pharmacology and Expt. Therapeutics, 299(3):951-959 (2001).
Jones et al., "Cannabinoid receptor systems: therapeutic targets for tumour intervention," Expert Opin Ther Targets, 7(6):749-758 (2003).
Kampa-Schittenhelm et al., Abstract. "Epigenetic hypomethylation of the 5'UTR of NADPH oxidase 4 (NOX4) by cannabidiol (CBD) results in increased protein expression, catalyzation of reactive oxygen species (ROS) and induction of apoptosisin acute leukemia," Oncol. Res. Treat., 40(Suppl 3):22 (2017), 1 page.
Kelly et al., "Tumor growth need not be driven by rare cancer stem cells," Science, 317(5836):337 (2007); https://www.science.org/doi/10.1126/science.1142596, 1 page.
Killestein et al., "Safety, tolerability, and efficacy of orally administered cannabinoids in MS," Neurology, 58(9):1404-1407 (2002).
Koppel et al., "Systematic review: Efficacy and safety of medical marijuana in selected neurologic disorders," American Academy of Neurology, 82:1556-1563 (2014).
Krajci et al., "Ultrastructure of nuclei of cisplatin-treated C6 glioma cells undergoing apoptosis," EP J. of Cell Biology, 79(5):365-376 (2000).
Lee et al., "Distinct Topographical Patterns of Spike-Wave Discharge in Transgenic and Pharmacologically Induced Absence Seizure Models," Exp Neurobiol, 28(4):474-484 (2019). doi: 10.5607/en.2019.28.4.474.
Levy et al., "Modulation of the metastatic frequency of a murine mammary adenocarcinoma by a synthetic cannabinoid drug," Seventh Annual Meeting of the American Association for Cancer Research, May 16-19, 1979, AACR Abstract, 2 pages.
Ligresti et al., "Antitumor activity of plant cannabinoids with emphasis on the effect of cannabidiol on human breast carcinoma," J Pharmacol Exp Ther., 318(3):1375-1387 (2006). Epub May 25, 2006.
Liu et al., "Enhancing the in vitro cytotoxic activity of Delta9-tetrahydrocannabinol in leukemic cells through a combinatorial approach," Leuk Lymphoma, 49(9):1800-1809 (2008).
Lopez-Valero et al., "Targeting Glioma Initiating Cells with A combined therapy of cannabinoids and temozolomide," Biochemical Pharmacology, 157:266-274 (2018).
Manni et al., "Obstructive Sleep Apnea in a Clinical Series of Adult Epilepsy Patients: Frequency and Features of the Comorbidity," Epilepsia, 44(6):836-840 (2003).
Massi et al., "Antitumour effects of cannabidiol, a nonpsychoactive cannabinoid, on human glioma cell lines," J Pharmacol Exp Ther., 308(3):838-845 (2004). Epub Nov. 14, 2003.
Mcallister et al., "Cannabidiol as a novel inhibitor of Id-I gene expression in aggressive breast cancer cells," Mol Cancer Ther., 6(11):2921-2927 (2007).
Mcallister et al., "Molecular Mechanisms of Cannabinoid Antitumor Activity," Research Grant proposal to Forbes Norris/MDA ALS Research Center, submitted as Exhibit A to Declaration by Sean D. McAllister and Pierre-Yves Desprez dated Nov. 26, 2012, filed in U.S. Appl. No. 12/600,553, 15 pages.
Mcallister, Excel data reporting results of experiments for "Molecular Mechanisms of Cannabinoid Antitumor Activity," Research Grant Proposal to Forbes orris/MDA ALS Research Center, submitted as Exhibit B to Declaration by Sean D. McAllister and Pierre-Yves Desprez dated Nov. 26, 2012, filed in U.S. Appl. No. 12/600,553, 1 page.
McGrath et al., "Randomized blinded controlled clinical trial to assess the effect of oral cannabidiol administration in addition to conventional antiepileptic treatment on seizure frequency in dogs with intractable idiopathic epilepsy," J Am Vet Med Assoc, 254(11):1301-1308 (2019).
Mechoulam et al., "Cannabidiol: an overview of some pharmacological aspects," J Clin Pharmacol, 42(1 Suppl):11S-19S (2002).
Nakagawa et al., "The combined effects of multiple chemotherapeutic agents for malignant glioma cells," J Neurooncol., 84:31-37 (2007).

(56) References Cited

OTHER PUBLICATIONS

[No Author Listed] Medicines Q&As: Cannabis-based medicinal products—potential drug interactions, prepared by UK Medicines Information (UKMi) pharmacists for NHS healthcare professionals, Nov. 29, 2018, 5 pages.

Nurmikko et al., "Sativex successfully treats neuropathic pain characterised by allodynia: a randomised, double-blind, placebo-controlled clinical trial," Pain, 133(1-3):210-220 (2007). Epub Nov. 7, 2007.

Perucca, "Clinically relevant drug interactions with antiepileptic drugs," British Journal of Clinical Pharmacology, 61(3):246-255 (2005).

Perucca, "Pharmacologic Advantages of Antiepileptic Drug Monotherapy," Epilepsia, 35(5):S6-S8 (1997).

Pisani, "Influence of co-medication on the metabolism of valproate," Pharmaceutish Weekblad Scientific Edition, 14(3A):108-113 (1992).

Podell et al., "2015 ACVIM Small Animal Consensus Statement on Seizure Management in Dogs," J Vet Intern Med, 30:477-490 (2016).

Portella et al., "Inhibitory effects of cannabinoid CB1 receptor stimulation on tumor growth and metastatic spreading: actions on signals involved in angiogenesis and metastasis," The FASEB Journal: Official Publication of the Federation of American Societies for Experimental Biology, 17(12):1771-1773 (2003).

Porter et al., "Report of a parent survey of cannabidiol-enriched cannabis use in pediatric treatment-resistant epilepsy," Epilepsy Behavior, 29(3):574-577 (2013).

Programme of the 10th Reunion Annual Sociedad Espanola de investigation sabre Cannabinoids (10th Annual Meeting of the Spanish Society for the Investigation of Cannabinoids), held in Santander, Nov. 26 to 28, 2009, downloaded from http:///www.seic.es/reunion-anual-seic on Oct. 25, 2016, 9 pages.

Robins et al., "Phase 2 trial of radiation plus high-dose tamoxifen for glioblastoma multiforme: RTOG protocol BR-0021," Neuro-Oncology, vol. 8, Issue 1, pp. 47-52 (2006).

Rosenthaler et al., "Differences in receptor binding affinity of several phytocannabinoids do not explain their effects on neural cell cultures," Neurotoxicol Teratol., 54:89-93 (2016).

Russo & Guy, "A tale of two cannabinoids: the therapeutic rationale for combining tetrahydrocannabinol and cannabidiol," Med Hypotheses, 66(2):234-236 (2006). Epub Oct. 4, 2005.

Sarfaraz et al., "Cannabinoid receptor as a novel target for the treatment of prostate cancer," Cancer Res., 65(5):1635-1641 (2005).

Scott et al., "Enhancing the Activity of Cannabidiol and Other Cannabinoids In Vitro Through Modifications to Drug Combinations and Treatment Schedules," Anticancer Research, 33(10):4373-4380 (2013).

Scott et al., "Anticancer effects of phytocannabinoids used with chemotherapy in leukaemia cells can be improved by altering the sequence of their administration," Int J Oncol., 51(1):369-377 (2017); doi: 10.3892/ijo.2017.4022. Epub May 29, 2017.

Singh et al., Cannabis extract treatment for terminal acute lymphoblastic leukemia with a Philadelphia chromosome mutation, Case Rep Oncol., 6(3):585-592 (2013). Epub Nov. 28, 2013; doi: 10.1159/000356446.

Snead, "The gamma-hydroxybutyrate model of absence seizures: correlation of regional brain levels of gamma-hydroxybutyric acid and gamma-butyrolactone with spike wave discharges," Neuropharmacology, 30(2):161-7 (1991). doi: 10.1016/0028-3908(91)90199-1.

Soroceanu et al., "The role of ID-1 in modulating brain tumor invasion and dispersal," Neuro-Oncology 11:564, Abstract No. 3, submitted as Exhibit C to Declaration of Sean McCallister and Pierre-Yves Desprez dated Nov. 26, 2012, filed in U.S. Appl. No. 12/600,553, 1 page.

Strasser et al., "Comparison of Orally Administered Cannabis Extract and Delta-9-Tetrahydrocannabinol in Treating Patients With Cancer-Related Anorexia-Cachexia Syndrome: A Multicenter, Phase III, Randomized, Double-Blind, Placebo-Controlled Clinical Trial From the Cannabis-In-Cachexia-Study-Group," J Clin Oncol., 24(21):3394-3400 (2006).

[No Author Listed] The United Kingdom Parliament, Select Committee on Science and Technology Ninth Report (1998) at http://www.parliament.the-stationery-office.co.uk/pa/ld199798/ldsctech/151/15101.htm, 43 pages.

[No Author Listed] The United Kingdom Parliament, Select Committee on Science and Technology Second Report (2001) at http://www.publications.parliament.uk/pa/ld200001/ldselect/ldsctech/50/5001.htm, 10 pages.

Torres et al., "A combined preclinical therapy of cannabinoids and temozolomide against glioma," Mol Cancer Ther., 10(1):90-103 (2011).

Tucker & Friedman, "Effects of cannabinoids on LI210 murine leukemia. 1. Inhibition of DNA synthesis," Res Commun Chem Pathol Pharmacol, 17(4):703-714 (1997).

Twelves et al., "A two-part safety and exploratory efficacy randomized double-blind, placebo-controlled study of a 1:1 ratio of the cannabinoids cannabidiol and delta-9-tetrahydrocannabinol (CBD:THC) plus dose-intense temozolomide in patients with recurrent glioblastoma multiforme (GBM)," Journal of Clinical Oncology, 35(15):2046 (2017). Abstract Only, 3 pages.

Vaccani et al., "Cannabidiol inhibits human glioma cell migration through a cannabinoid receptor-independent mechanism," Br J Pharmacol., 144(8):1032-1036 (2007).

Velasco et al., "Hypothesis: cannabinoid therapy for the treatment of gliomas?" Neuropharmacology, 47:315-323 (2004).

Verbraecken et al., "Body surface area in normal-weight, over-weight, and obese adults. A comparison study," Metabolism, 55(4):515-524 (2006).

Volk et al., "The efficacy and tolerability of levetiracetam in pharmacoresistant epileptic dogs," Vet J, 176:310-319 (2008).

Volk et al., "International Veterinary Epilepsy Task Force consensus reports on epilepsy definition, classification and terminology," BMC Vet Res, 11:182 (2015), 2 pages.

Whalley, "Cannabis and epilepsy from recreational use to therapeutic use," University of Reading, 2007, 18 pages.

Wiley et al., "Cytosine arabinoside transport and metabolism in acute leukemias and T cell lymphoblastic lymphoma," Journal of Clinical Investigation, 75(2):632-642 (1985).

Wilson et al., "Can pharmaco-electroencephalography help improve survival of central nervous system drugs in early clinical development?" Drug Discov Today, 19(3):282-8 (2014). doi: 10.1016/j.drudis.2013.08.001.

Zhongshi et al., "The New Development of Anti-tumor Drug. Evaluation and Analysis of Drug-Use in Hospitals of China," 4(1), 2004, 8 pages.

U.S. Appl. No. 15/640,033, filed Jun. 30, 2017.
U.S. Appl. No. 16/768,241, filed May 29, 2020.
U.S. Appl. No. 16/959,354, filed Jun. 30, 2020.
U.S. Appl. No. 16/935,005, filed Jul. 21, 2020.
U.S. Appl. No. 17/012,448, filed Sep. 4, 2020.
U.S. Appl. No. 17/050,956, filed Oct. 27, 2020.
U.S. Appl. No. 17/102,109, filed Nov. 23, 2020.
U.S. Appl. No. 17/231,625, filed Apr. 15, 2021.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/606,370, filed Oct. 25, 2021.
U.S. Appl. No. 17/611,824, filed Nov. 16, 2021.
U.S. Appl. No. 17/548,232, filed Dec. 10, 2021.
U.S. Appl. No. 17/576,868, filed Jan. 14, 2022.
U.S. Appl. No. 17/627,946, filed Jan. 18, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/768,048, filed Apr. 11, 2022.
U.S. Appl. No. 17/770,435, filed Apr. 20, 2022.

(56) References Cited

OTHER PUBLICATIONS

U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/744,224, filed May 13, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/841,167, filed Jun. 15, 2022.
U.S. Appl. No. 17/786,949, filed Jun. 17, 2022.
U.S. Appl. No. 17/853,367, filed Jun. 29, 2022.
U.S. Appl. No. 17/817,753, filed Aug. 5, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,843, filed Jan. 17, 2023.
U.S. Appl. No. 18/005,845, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,868, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,121, filed Jan. 19, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18,006,131, filed Jan. 19, 2023.
U.S. Appl. No. 18,006,133, filed Jan. 19, 2023.
U.S. Appl. No. 18/161,603, filed Jan. 30, 2023.
U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/311,221, filed May 2, 2023.
U.S. Appl. No. 18/256,307, filed Jun. 7, 2023.
U.S. Appl. No. 18/257,373, filed Jun. 14, 2023.
U.S. Appl. No. 18/257,537, filed Jun. 14, 2023.
U.S. Appl. No. 18/257,479, filed Jun. 14, 2023.
U.S. Appl. No. 18/258,485, filed Jun. 20, 2023.
U.S. Appl. No. 18/446,405, filed Aug. 8, 2023.
U.S. Appl. No. 18/546,254, filed Aug. 11, 2023.
U.S. Appl. No. 18/548,003, filed Aug. 25, 2023.
U.S. Appl. No. 18/477,467, filed Sep. 28, 2023.
U.S. Appl. No. 18/479,671, filed Oct. 2, 2023.
U.S. Appl. No. 18/560,316, filed Nov. 10, 2023.
U.S. Appl. No. 18/560,337, filed Nov. 10, 2023.
U.S. Appl. No. 18/560,341, filed Nov. 10, 2023.
U.S. Appl. No. 18/560,346, filed Nov. 10, 2023.
U.S. Appl. No. 18/526,795, filed Dec. 1, 2023.
U.S. Appl. No. 18/545,754, filed Dec. 19, 2023.
U.S. Appl. No. 18/292,844, filed Jan. 26, 2024.
U.S. Appl. No. 18/597,717, filed Mar. 6, 2024.
U.S. Appl. No. 15/640,033, filed Jun. 30, 2017; Inventor(s): Jitinder Wilkhu et al.
U.S. Appl. No. 16/768,241, filed May 29, 2020; Inventor(s): Geoffrey Guy et al.
U.S. Appl. No. 16/959,354, filed Jun. 30, 2020; Inventor(s): Jitinder Wilkhu et al.
U.S. Appl. No. 16/935,005, filed Jul. 21, 2020; Inventor(s): Geoffrey Guy et al.
U.S. Appl. No. 17/012,448, filed Sep. 4, 2020; Inventor(s): Benjamin Whalley et al.
U.S. Appl. No. 17/050,956, filed Oct. 27, 2020; Inventor(s): Geoffrey Guy et al.
U.S. Appl. No. 17/102,109, filed Nov. 23, 2020; Inventor(s): Guillermo Velasco Diez et al.
U.S. Appl. No. 17/231,625, filed Apr. 15, 2021; Inventor(s): Stephen Wright et al.
U.S. Appl. No. 17/296,066, filed May 21, 2021; Inventor(s): Geoffrey Guy et al.
U.S. Appl. No. 17/296,076, filed May 21, 2021; Inventor(s): Geoffrey Guy et al.
U.S. Appl. No. 17/424,682, filed Jul. 21, 2021; Inventor(s): geoffrey Guy et al.
U.S. Appl. No. 17/426,442, filed Jul. 28, 2021; Inventor(s): Geoffrey Guy et al.
U.S. Appl. No. 17/406,401, filed Aug. 19, 2021; Inventor(s): Jitinder Wilkhu et al.
U.S. Appl. No. 17/435,892, filed Sep. 2, 2021; Inventor(s): Geoffrey Guy et al.
U.S. Appl. No. 17/606,370, filed Oct. 25, 2021; Inventor(s): Geoffrey Guy et al.
U.S. Appl. No. 17/611,824, filed Nov. 16, 2021; Inventor(s): Geoffrey Guy et al.
U.S. Appl. No. 17/548,232, filed Dec. 10, 2021; Inventor(s): Stephen Wright et al.
U.S. Appl. No. 17/576,868, filed Jan. 14, 2022; Inventor(s): Benjamin Whalley et al.
U.S. Appl. No. 17/627,946, filed Jan. 18, 2022; Inventor(s): Alan James Silcock et al.
U.S. Appl. No. 17/631,069, filed Jan. 28, 2022; Inventor(s): Geoffrey Guy et al.
U.S. Appl. No. 17/638,629, filed Feb. 25, 2022; Inventor(s): Benjamin Whalley et al.
U.S. Appl. No. 17/689,607, filed Mar. 8, 2022; Inventor(s): Geoffrey Guy et al.
U.S. Appl. No. 17/689,245, filed Mar. 8, 2022; Inventor(s): Harshit Shah.
U.S. Appl. No. 17/768,048, filed Apr. 11, 2022; Inventor(s): Geoffrey Guy et al.
U.S. Appl. No. 17/770,435, filed Apr. 20, 2022; Inventor(s): Geoffrey Guy et al.
U.S. Appl. No. 17/770,436, filed Apr. 20, 2022; Inventor(s): Geoffrey Guy et al.
U.S. Appl. No. 17/771,184, filed Apr. 22, 2022; Inventor(s): Geoffrey Guy et al.
U.S. Appl. No. 17/771,190, filed Apr. 22, 2022; Inventor(s): Geoffrey Guy et al.
U.S. Appl. No. 17/771,195, filed Apr. 22, 2022; Inventor(s): Geoffrey Guy et al.
U.S. Appl. No. 17/771,183, filed Apr. 22, 2022; Inventor(s): Geoffrey Guy et al.
U.S. Appl. No. 17/744,224, filed May 13, 2022; Inventor(s): Geoffrey Guy et al.
U.S. Appl. No. 17/777,734, filed May 18, 2022; Inventor(s): Geoffrey Guy et al.
U.S. Appl. No. 17/777,677, filed May 18, 2022; Inventor(s): Geoffrey Guy et al.
U.S. Appl. No. 17/777,681, filed May 18, 2022; Inventor(s): Geoffrey Guy et al.
U.S. Appl. No. 17/841,167, filed Jun. 15, 2022; Inventor(s): Geoffrey Guy et al.
U.S. Appl. No. 17/786,949, filed Jun. 17, 2022; Inventor(s): Alan James Silcock et al.
U.S. Appl. No. 17/853,367, filed Jun. 29, 2022; Inventor(s): Geoffrey Guy et al.
U.S. Appl. No. 17/817,753, filed Aug. 5, 2022; Inventor(s): Volker Knappertz et al.
U.S. Appl. No. 18/002,437, filed Dec. 19, 2022; Inventor(s): Jie Li et al.
U.S. Appl. No. 18/005,838, filed Jan. 17, 2023; Inventor(s): Daniel Adam Checketts et al.
U.S. Appl. No. 18/005,841, filed Jan. 17, 2023; Inventor(s): Daniel Adam Checketts et al.

(56) References Cited

OTHER PUBLICATIONS

U.S. Appl. No. 18/005,843, filed Jan. 17, 2023; Inventor(s): Daniel Adam Checketts et al.
U.S. Appl. No. 18/005,845, filed Jan. 17, 2023; Inventor(s): Daniel Adam Checketts et al.
U.S. Appl. No. 18/005,847, filed Jan. 17, 2023; Inventor(s): Daniel Adam Checketts et al.
U.S. Appl. No. 18/005,848, filed Jan. 17, 2023; Inventor(s): Daniel Adam Checketts et al.
U.S. Appl. No. 18/005,851, filed Jan. 18, 2023; Inventor(s): Daniel Adam Checketts et al.
U.S. Appl. No. 18/005,852, filed Jan. 18, 2023; Inventor(s): Daniel Adam Checketts et al.
U.S. Appl. No. 18/005,853, filed Jan. 18, 2023; Inventor(s): Daniel Adam Checketts et al.
U.S. Appl. No. 18/005,868, filed Jan. 18, 2023; Inventor(s): Daniel Adam Checketts et al.
U.S. Appl. No. 18/005,959, filed Jan. 18, 2023; Inventor(s): Daniel Adam Checketts et al.
U.S. Appl. No. 18/005,960, filed Jan. 18, 2023; Inventor(s): Daniel Adam Checketts et al.
U.S. Appl. No. 18/005,961, filed Jan. 18, 2023; Inventor(s): Daniel Adam Checketts et al.
U.S. Appl. No. 18/006,121, filed Jan. 19, 2023; Inventor(s): Daniel Adam Checketts et al.
U.S. Appl. No. 18/006,125, filed Jan. 19, 2023; Inventor(s): Daniel Adam Checketts et al.
U.S. Appl. No. 18/006,127, filed Jan. 19, 2023; Inventor(s): Daniel Adam Checketts et al.
U.S. Appl. No. 18/006,129, filed Jan. 19, 2023; Inventor(s): Daniel Adam Checketts et al.
U.S. Appl. No. 18,006,131, filed Jan. 19, 2023; Inventor(s): Daniel Adam Checketts et al.
U.S. Appl. No. 18,006,133, filed Jan. 19, 2023; Inventor(s): Daniel Adam Checketts et al.
U.S. Appl. No. 18/161,603, filed Jan. 30, 2023; Inventor(s): William Hind et al.
U.S. Appl. No. 18/170,235, filed Feb. 16, 2023; Inventor(s): Geoffrey Guy et al.
U.S. Appl. No. 18/043,810, filed Mar. 2, 2023; Inventor(s): Michael Simon Loft et al.
U.S. Appl. No. 18/044,941, filed Mar. 10, 2023; Inventor(s): Kevin James Craig et al.
U.S. Appl. No. 18/245,856, filed Mar. 17, 2023; Inventor(s): Kevin James Craig et al.
U.S. Appl. No. 18/186,792, filed Mar. 20, 2023; Inventor(s): Geoffrey Guy et al.
U.S. Appl. No. 18/311,221, filed May 2, 2023; Inventor(s): Geoffrey Guy et al.
U.S. Appl. No. 18/256,307, filed Jun. 7, 2023; Inventor(s): Daniel Adam Checketts et al.
U.S. Appl. No. 18/257,373, filed Jun. 14, 2023; Inventor(s): Alan James Silcock et al.
U.S. Appl. No. 18/257,537, filed Jun. 14, 2023; Inventor(s): Alan James Silcock et al.
U.S. Appl. No. 18/257,479, filed Jun. 14, 2023; Inventor(s): Karen Ka-Yen Tse et al.
U.S. Appl. No. 18/258,485, filed Jun. 20, 2023; Inventor(s): Kevin James Craig et al.
U.S. Appl. No. 18/446,405, filed Aug. 8, 2023; Inventor(s): Geoffrey Guy et al.
U.S. Appl. No. 18/546,254, filed Aug. 11, 2023; Inventor(s): Karen Ka-Yen Tse.
U.S. Appl. No. 18/548,003, filed Aug. 25, 2023; Inventor(s): Volker Knappertz et al.
U.S. Appl. No. 18/477,467, filed Sep. 28, 2023; Inventor(s): Jitinder Wilkhu et al.
U.S. Appl. No. 18/479,671, filed Oct. 2, 2023; Inventor(s): Alan James Silcock et al.
U.S. Appl. No. 18/560,316, filed Nov. 10, 2023; Inventor(s): Alan James Silcock et al.
U.S. Appl. No. 18/560,337, filed Nov. 10, 2023; Inventor(s): Alan James Silcock et al.
U.S. Appl. No. 18/560,341, filed Nov. 10, 2023; Inventor(s): Alan James Silcock et al.
U.S. Appl. No. 18/560,346, filed Nov. 10, 2023; Inventor(s): Alan James Silcock et al.
U.S. Appl. No. 18/526,795, filed Dec. 1, 2023; Inventor(s): Geoffrey Guy et al.
U.S. Appl. No. 18/545,754, filed Dec. 19, 2023; Inventor(s): Geoffrey Guy et al.
U.S. Appl. No. 18/292,844, filed Jan. 26, 2024; Inventor(s): Volker Knappertz.
U.S. Appl. No. 18/597,717, filed Mar. 6, 2024; Inventor(s): Jonathan Oliver Whitehouse et al.
Rana et al., "Cannabidiol and Sodium Valproate Demonstrate Pharmacodynamic Synergism in an Acute Mouse 3.479 Model of Generalised Seizures," Poster, presented at The American Epilepsy Society Annual Meeting 2023; Dec. 1-5, 2023; Orlando, FL, USA, 1 page.

\* cited by examiner

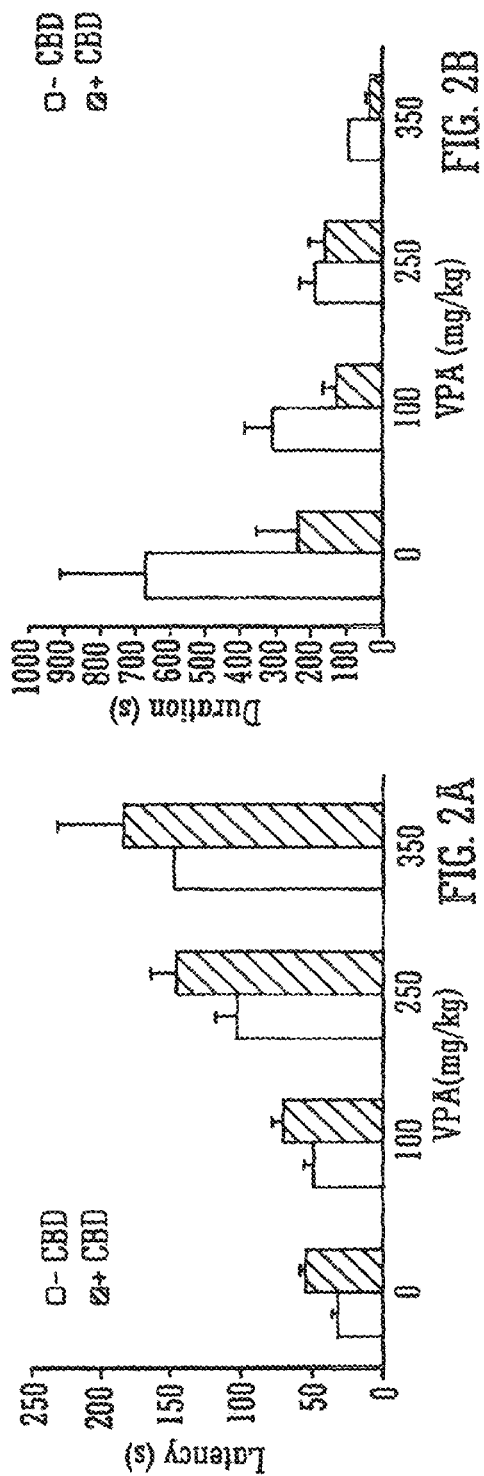
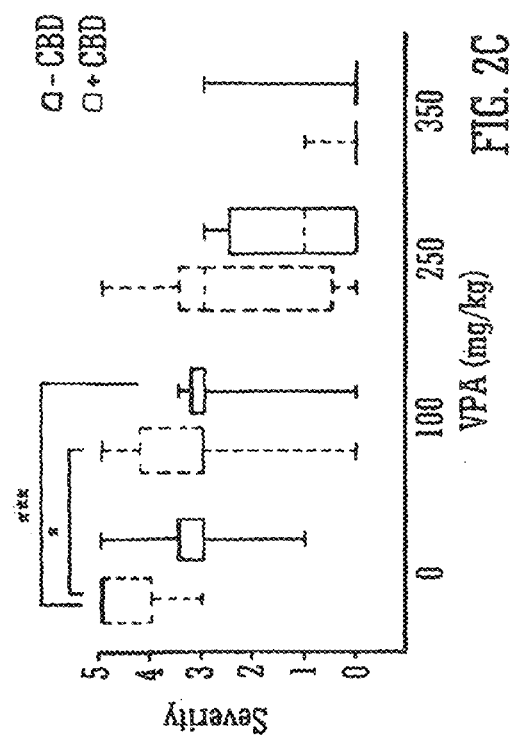
FIG. 2A
FIG. 2B
FIG. 2C

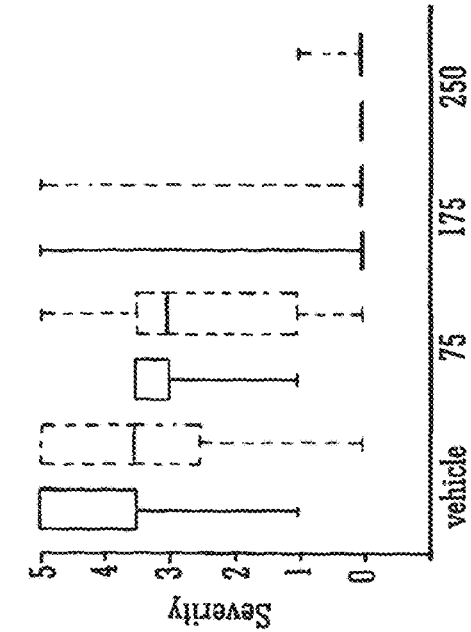
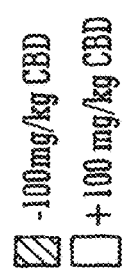
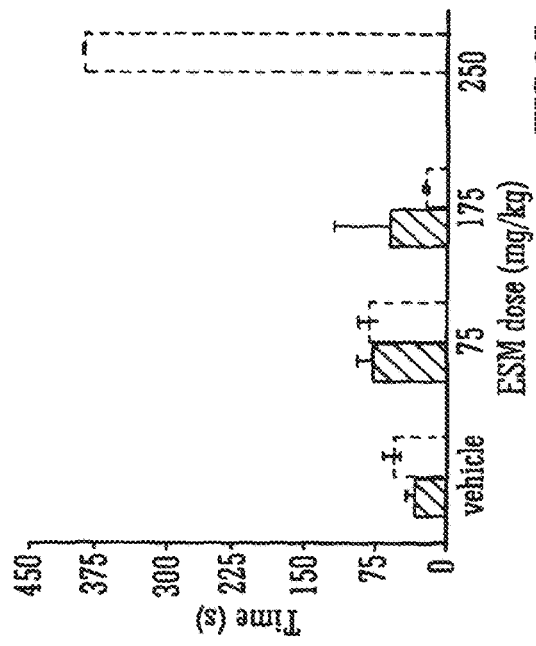
FIG. 3A
FIG. 3B
FIG. 3C

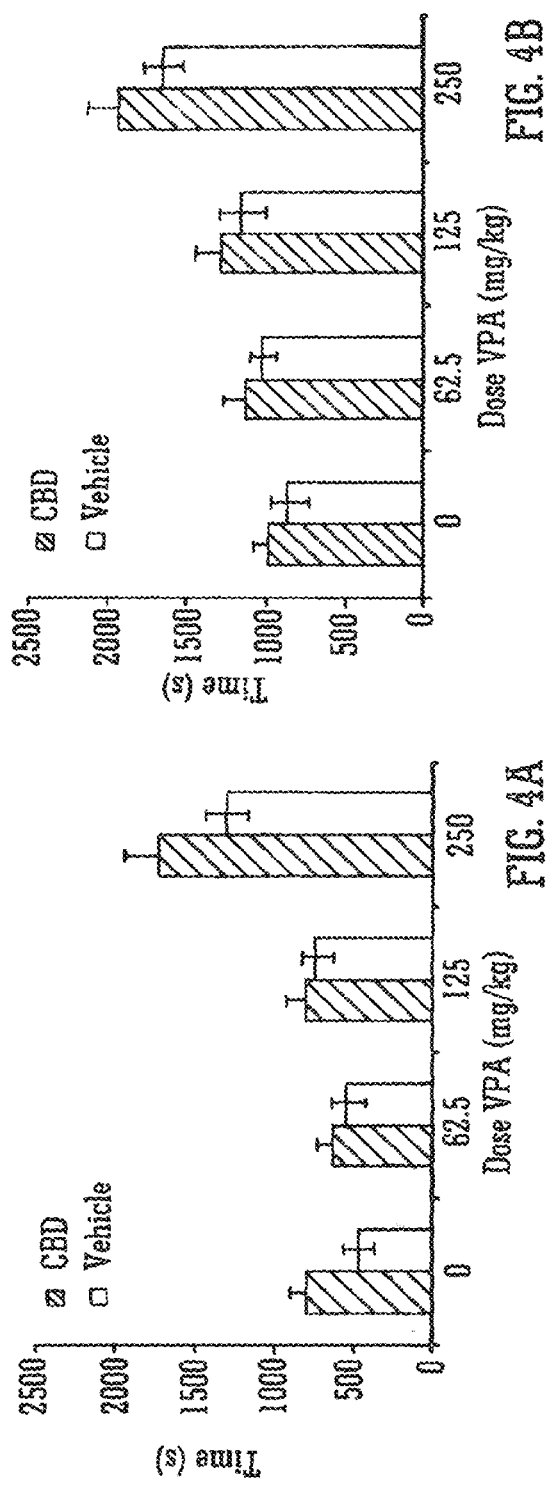

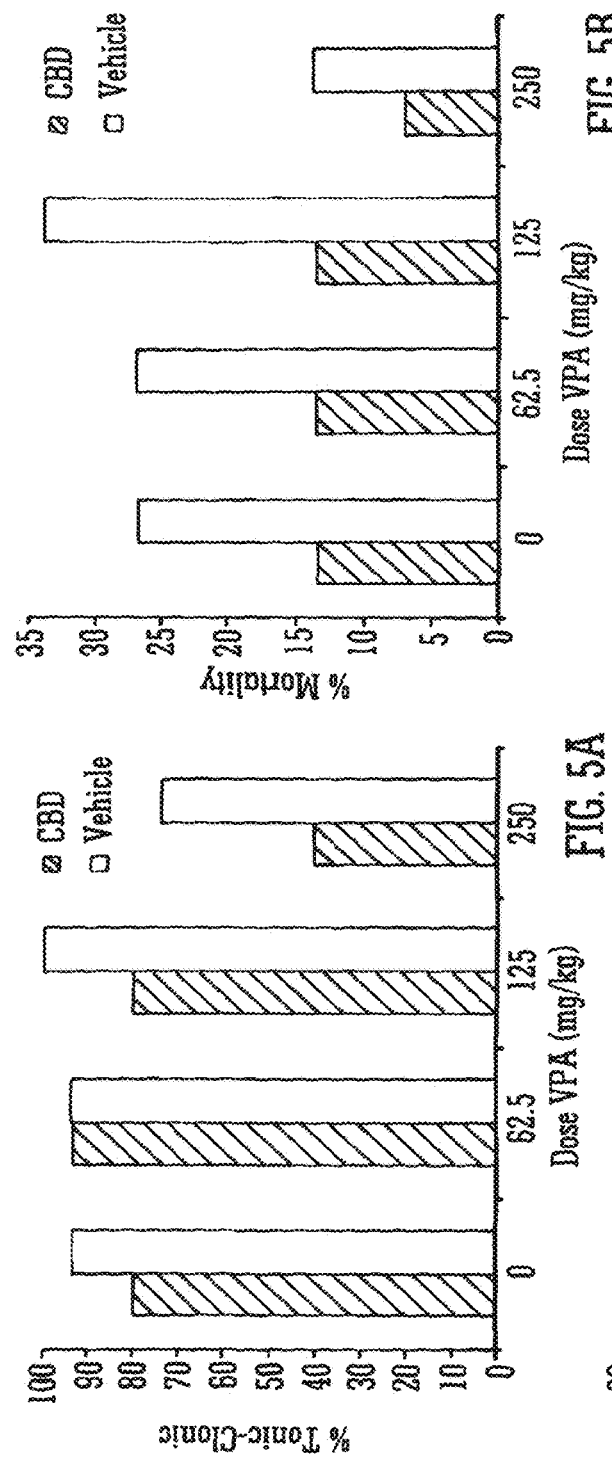

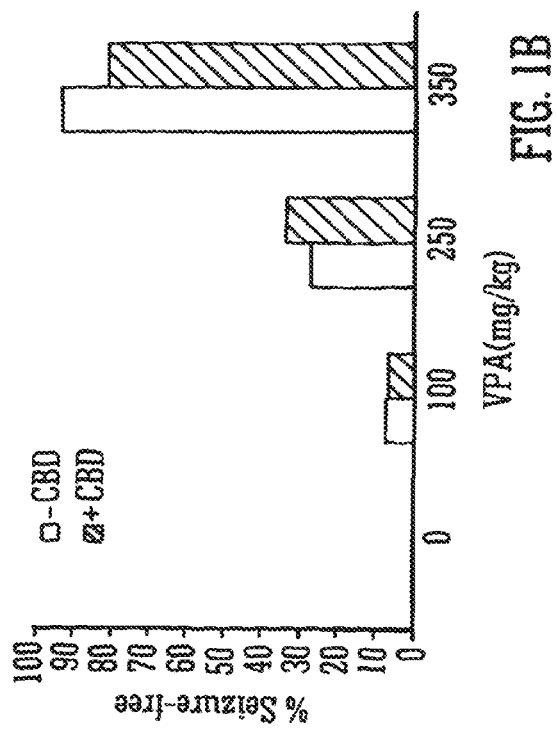
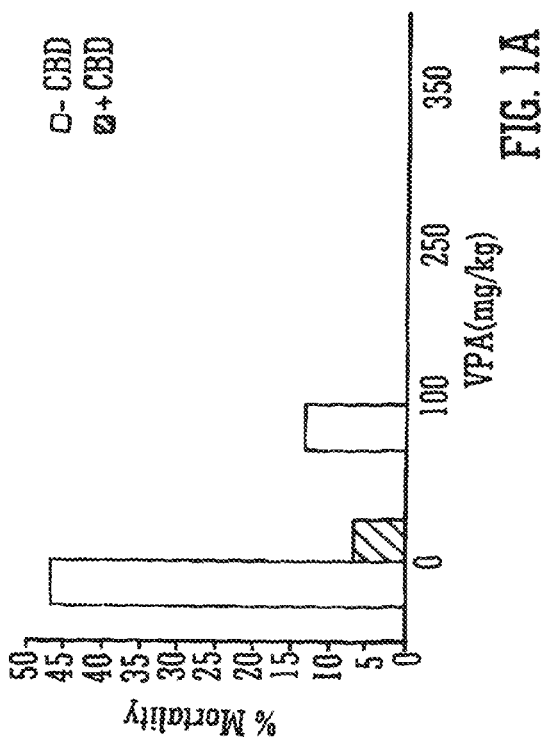
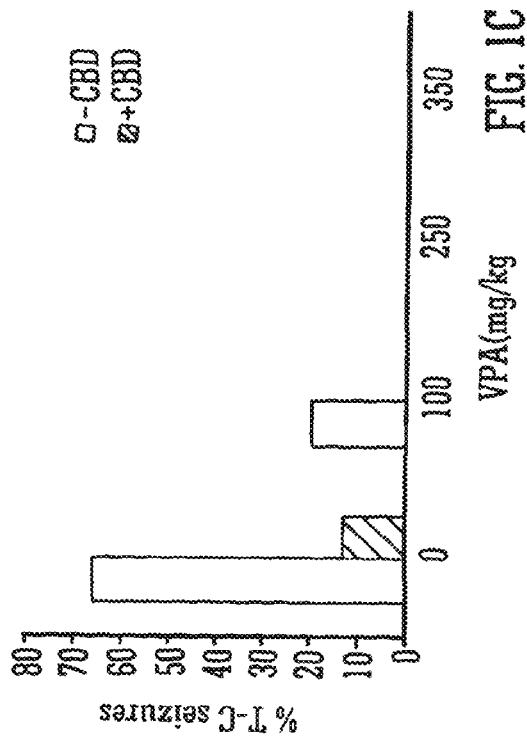

USE OF THE PHYTOCANNABINOID CANNABIDIOL (CBD) IN COMBINATION WITH A STANDARD ANTI-EPILEPTIC DRUG (SAED) IN THE TREATMENT OF EPILEPSY

CROSS-REFERENCE TO RELATED APPLICATIONS

This application is a Continuation of U.S. patent application Ser. No. 13/977,766, filed Jul. 1, 2013, which is a U.S. National Stage Application under 35 U.S.C. § 371 of International Application No. PCT/GB2012/050002, filed Jan. 3, 2012, which claims priority to Great Britain Patent Application No. 1100043.7, filed Jan. 4, 2011 the contents of which are incorporated herein by reference in their entirety.

This Invention relates to the use of the phytocannabinoid cannabidiol (CBD) in combination with a standard anti-epileptic drug (SAED). Preferably the CBD is used in combination with a SAED with a mechanism of action which acts via sodium or calcium channels, more preferably one which:
- modifies low-threshold or transient neuronal calcium currents, as exemplified by ethosuximide; or
- reduces high-frequency neuronal firing and sodium-dependent action potentials and may additionally enhance GABA effects, as exemplified by valproate.

BACKGROUND

Epilepsy is a chronic neurological disorder presenting a wide spectrum of diseases that affect approximately 50 million people worldwide (Sander, 2003). Advances in the understanding of the body's internal 'endocannabinoid' system has lead to the suggestion that *cannabis*-based medicines may have the potential to treat this disorder of hyperexcitability in the central nervous system (Mackie, 2006, Wingerchuk, 2004, Alger, 2006).

*Cannabis* has been ascribed both pro-convulsant (Brust et al., 1992) and anti-convulsant effects. Therefore, it remains to determine whether cannabinoids represent a yet to be unmasked therapeutic anticonvulsant or, conversely, a potential risk factor to recreational and medicinal users of *cannabis* (Ferdinand et al., 2005).

In 1975 Consroe et al. described the case of young man whose standard treatment (phenobarbitol and phenytoin), didn't control his seizures. When he began to smoke *cannabis* socially he had no seizures. However when he took only *cannabis* the seizures returned. They concluded that 'marihuana may possess an anti-convulsant effect in human epilepsy'.

A study by Ng (1990) involved a larger population of 308 epileptic patients who had been admitted to hospital after their first seizure. They were compared to a control population of 294 patients who had not had seizures, and it was found that using *cannabis* seemed to reduce the likelihood of having a seizure. However this study was criticized in an Institute of Medicine report (1999) which claimed it was 'weak', as 'the study did not include measures of health status prior to hospital admissions and differences in their health status might have influenced their drug use' rather than the other way round.

Three controlled trials have investigated the anti-epilepsy potential of cannabidiol. In each, cannabidiol was given in oral form to sufferers of generalised grand mal or focal seizures.

Cunha et al (1980) reported a study on 16 grand mal patients who were not doing well on conventional medication. They received their regular medication and either 200-300 mg of cannabidiol or a placebo. Of the patients who received CBD, 3 showed complete improvement, 2 partial, 2 minor, while 1 remained unchanged. The only unwanted effect was mild sedation. Of the patients who received the placebo, 1 improved and 7 remained unchanged.

Ames (1986) reported a less successful study in which 12 epileptic patients were given 200-300 mg of cannabidiol per day, in addition to standard antiepileptic drugs. There seemed to be no significant improvement in seizure frequency.

Trembly et al (1990) performed an open trial with a single patient who was given 900-1200 mg of cannabidiol a day for 10 months. Seizure frequency was markedly reduced in this single patient.

In addition to the disclosures suggesting CBD may be beneficial there is a report (Davis & Ramsey) of tetrahydrocannabinol (THC) being administered to 5 institutionalized children who were not responding to their standard treatment (phenobarbital and phenoytin). One became entirely free of seizures, one became almost completely free of seizures, and the other three did no worse than before.

In WO 2006/054057 it is suggested that the cannabinoid Tetrahydrocannabivarin (THCV) may behave as anti epileptic, something confirmed by Thomas et al 2005.

In addition WO 2009/007697 describes a THCV and CBD pharmaceutical formulation. Such a formulation is suggested to be of use in many different types of diseases including epilepsy.

However, there are more than forty recognisable types of epileptic syndrome partly due to seizure susceptibility varying from patient to patient (McCormick and Contreras, 2001, Lutz, 2004) and a challenge is finding drugs effective against these differing types.

Neuronal activity is a prerequisite for proper brain function. However, disturbing the excitatory—inhibitory equilibrium of neuronal activity may induce epileptic seizures. These epileptic seizures can be grouped into two basic categories:
  a. Partial, and
  b. Generalised seizures.

Partial seizures originate in specific brain regions and remain localised—most commonly the temporal lobes (containing the hippocampus), whereas generalised seizures appear in the entire forebrain as a secondary generalisation of a partial seizure (McCormick and Contreras, 2001, Lutz, 2004). This concept of partial and generalised seizure classification did not become common practice until the International League Against Epilepsy published a classification scheme of epileptic seizures in 1969 (Merlis, 1970, Gastaut, 1970, Dreifuss et al., 1981).

The International League Against Epilepsy further classified partial seizures, separating them into simple and complex, depending on the presence or the impairment of a consciousness state (Dreifuss et al., 1981).

The league also categorized generalised seizures into numerous clinical seizure types, some examples of which are outlined below:

Absence seizures occur frequently, having a sudden onset and interruption of ongoing activities. Additionally, speech is slowed or impeded with seizures lasting only a few seconds (Dreifuss et al., 1981).

Tonic-clonic seizures, often known as "grand mal", are the most frequently encountered of the generalised seizures (Dreifuss et al., 1981). This generalised seizure type has two stages: tonic muscle contractions which then give way to a clonic stage of convulsive movements. The patient remains unconscious throughout the seizure and for a variable period of time afterwards.

Atonic seizures, known as "drop attacks", are the result of sudden loss of muscle tone to either a specific muscle, muscle group or all muscles in the body (Dreifuss et al., 1981).

The onset of epileptic seizures can be life threatening with sufferers also experiencing long-term health implications (Lutz, 2004). These implications may take many forms:
- mental health problems (e.g. prevention of normal glutamatergic synapse development in childhood);
- cognitive deficits (e.g. diminishing ability of neuronal circuits in the hippocampus to learn and store memories); and
- morphological changes (e.g. selective loss of neurons in the CA1 and CA3 regions of the hippocampus in patients presenting mesial temporal lobe epilepsy as a result of excitotoxicity) (Swann, 2004, Avoll et al., 2005)

It is noteworthy that epilepsy also greatly affects the lifestyle of the sufferer—potentially living in fear of consequential injury (e.g. head injury) resulting from a grand mal seizure or the inability to perform daily tasks or the inability to drive a car unless having had a lengthy seizure-free period (Fisher et al., 2000).

There are many different standard anti-epileptic drugs available at the present time including: acetozolamide, carbamazepine, clobazam, clonazepam, ethosuximide, eslicarbazepine acetate, gabapentin, lacosamide, lamotriquine, levetiracetam, oxcarbazepine, Phenobarbital, phenytoin, pregabalin, primidone, rufinamide, sodium valproate, tiagabine, topiramate, valproate, vigabatrin, and zonisamide.

The mode of action of some of these is understood and for others is unknown. Some modes of action are set out in Table 1 below: (Adapted from: Schachter S C. Treatment of seizures. In: Schachter S C, Schomer D L, eds. The comprehensive evaluation and treatment of epilepsy. San Diego, CA: Academic Press; 1997. p. 61-74)

TABLE 1

| Antiepileptic drug | Mechanism of action | Sodium or calcium channel involvement |
|---|---|---|
| Barbiturates: primidone (Mysoline), phenobarbital | Enhances GABAergic inhibition | |
| Carbamazepine (Tegretol, Tegretol-XR, Carbatrol) | Inhibits voltage-dependent sodium channels | Sodium |
| Ethosuximide (Zarontin) | Modifies low-threshold or transient neuronal calcium currents | Calcium |
| Felbamate (Felbatol) | Unknown | |
| Gabapentin (Neurontin) | Unknown | |
| Lamotrigine (Lamictal) | Inhibits voltage-dependent sodium channels, resulting in decreased release of the excitatory neurotransmitters glutamate and aspartate | Sodium |
| Phenytoin (Dilantin, Phenytek) | Blocks sodium-dependent action potentials; reduces neuronal calcium uptake | Sodium/ Calcium |
| Valproate (Depakote, Depakote ER, Depakene, valproic acid) | Reduces high-frequency neuronal firing and sodium-dependent action potentials; enhances GABA effects | Sodium |

Three well-established and extensively used in vivo mode is of epilepsy are:
- pentylenetetrazole-induced (PTZ) model of generalised seizures (Obay et al., 2007, Rauca et al., 2004);
- pilocarpine-induced model of temporal lobe (i.e. hippocampus) seizures (Pereira et al., 2007); and
- penicillin-induced model of partial seizures (Bostanci and Bagirici, 2006).

These provide a range of seizure and epilepsy models, essential for therapeutic research in humans.

The application WO 02/064109 describes a pharmaceutical formulation where the cannabinoids THC and CBD are used. The application goes on to state that the propyl analogs of these cannabinoids may also be used in the formulation. Since this application was written it has been shown that THCV behaves in a very different manner to THC and therefore the assumption that the propyl analogs of cannabinoids behave in a similar manner to their pentyl counterparts is now not valid.

The application GB0911580.9 describes the use of THCV for the treatment of generalised seizures, also described is the use of the cannabinoid CBD in combination with the THCV.

It is an object of the present invention to identify novel drug combinations which will enhance or otherwise offer benefits in the use of SAED's. The use of a combination may allow for lower doses of SAED's to be used then is conventional.

BRIEF SUMMARY OF THE DISCLOSURE

In accordance with a first aspect of the present invention there is provided cannabidiol, (CBD), at a dose of greater than 300 mg/day, in combination with a standard anti-epileptic drug (SAED) which acts via sodium or calcium channels, for use in the treatment of epilepsy.

The SAED which acts via sodium or calcium channels may be exemplified by a drug which:
- modifies low-threshold or transient neuronal calcium currents, such as, ethosuximide; or
- reduces high-frequency neuronal firing and sodium-dependent action potentials (and may additionally enhance GABA effects), such as, valproate;

In contrast, a SAED which (solely) enhances GABAergic inhibition (as opposed to acting via sodium or calcium channels), such as, phenobarbital, does not appear to provide benefits in combination with CBD, when tested in a pilocarpine model. Thus, the selective benefits of CBD with e.g. ethosuximide and valporate (SAED's with defined and distinct mechanisms of actions involving calcium and sodium channels) could not be anticipated.

In accordance with a second aspect of the present invention there is provided the use of cannabidiol (CBD), at a dose of greater than 300 mg/day, in combination with a standard anti-epileptic drug (SAED) which acts via sodium or calcium channels, in the manufacture of a medicament for use in the treatment of epilepsy.

In accordance with a third aspect of the present invention there is provided a method for the treatment of epilepsy, which comprises administering to a subject in need thereof cannabidiol (CBD), at a dose of greater than 300 mg/day, in combination with a standard anti-epileptic drug (SAED) which acts via sodium or calcium channels.

In accordance with a forth aspect of the present invention there is provided a combination product comprising cannabidiol (CBD), at a dose of greater than 300 mg/day, and a standard anti-epileptic drug (SAED) which acts via sodium or calcium channels.

The respective drugs may be packaged separately with instructions to be taken in combination or may be formulated as a single use product.

Preferably the standard anti-epileptic drug acting via sodium or calcium channels is taken from the group consisting of: ethosuximide and valproate.

Preferably the type of epilepsy to be treated is a generalised seizure or a temporal lobe seizure.

The combination may prove beneficial in one or more of the following:
  a. reducing the incidence of tonic-clonic seizures;
  b. Increasing the amount of time a patient is seizure free;
  c. increasing the latency to onset of seizure;
  d. decreasing the overall duration of the seizure; and
  e. reducing the severity and mortality of the seizures.

Thus, the combinations are particularly well suited in the treatment of conditions generally considered refractory to existing medication. The combinations would also appear to allow for the use of lower doses of the SAED's than would be used were the SAED to be used alone.

In one embodiment the CBD is used with one or more therapeutically effective other phytocannabinoid(s).

Preferably the one or more therapeutically effective other phytocannabinoid is THCV and/or CBDV.

In one embodiment the CBD is in an isolated form.

In a further embodiment the CBD is in the form of a botanical drug substance.

BRIEF DESCRIPTION OF THE DRAWINGS

By way of example only, a number of embodiments of the invention are described hereinafter with reference to the accompanying drawings, in which FIG. 1 A-C shows the effect of CBD at 100 mg/kg in combination with valproate on PTZ-induced seizures;

FIG. 2 A-C shows the effect of CBD and valproate on latency, duration and severity of PTZ-induced seizures;

FIG. 3 A-C shows the effect of CBD at 100 mg/kg and ethosuximide on PTZ-induced seizures;

FIG. 4 A-C shows the anti-convulsant effects of 100 mg/kg CBD in combination with valproate on the development of pilocarpine-induced seizures; and FIG. 5 A-C shows the effect of 100 mg/kg CBD in combination with valproate on the development of pilocarpine-induced seizure and mortality incidence.

Legend to FIG. 1: A: % mortality with (black bars) and without 100 mg/kg CBD (white bars). B: % seizure free with (black bars) and without 100 mg/kg CBD (white bars). C: % of animals that developed the most severe (tonic-clonic) seizures with (black bars) and without 100 mg/kg CBD (white bars).

Legend to FIG. 2: A: latency to seizure onset; B: duration of seizure activity of those animals that survived; C: median seizure severity.

Legend to FIG. 3: A: latency to onset of seizures at different doses of ethosuximide without (black) or with (grey unfilled) 100 mg/kg CBD. B: Seizure severity. C: Percentage mortalities, key as in A.

Legend to FIG. 4: Mean latency to onset (A). development of bilateral seizures (B) and tonic-clonic seizures (C).

Legend to FIG. 5: A: Proportion (%) of animals in each dose group that exhibited fully developed tonic-clonic seizures. B: Proportion (%) of animals in each dose group that died. C: Proportion (%) of animals in each dose group that were seizure free.

DETAILED DESCRIPTION

The examples below describe the use of isolated CBD in combination with standard anti-epileptic drugs (SAEDs) in two different models of epilepsy, namely the PTZ-induced seizure model and the pilocarpine-induced seizure model. The SAEDs used in these examples are ethosuximide, valproate and Phenobarbital (Pilocarpine model only). It is important to note that there are many different SAEDs available and the drugs chosen for these experiments provide a general overview of how the phytocannabinoid CBD is able to work in combination with different classes of drugs used in the treatment of epilepsy.

Example 1

The Use of the Phytocannabinoid CBD in Combination with a Standard Anti-Epileptic Drug (SAED) in the PTZ-Model of Epilepsy Methodology:

Animals:

Male Wistar rats (P24-29; 75-110 g) were used to assess the effects of the phytocannabinoid CBD in combination with SAEDs in the PTZ model of generalised seizures. Animals were habituated to the test environment, cages, injection protocol and handling prior to experimentation. Animals were housed in a room at 21° C. on a 12 hour light: dark cycle (lights on 0900) in 50% humidity, with free access to food and water.

The human dose equivalent (HED) can be estimated using the following formula:

$$HED = \text{Animal dose (mg/kg) multiplied by } \frac{\text{Animal } K_m}{\text{Human } K_m}$$

The $K_m$ for a rat is 6 and the $K_m$ for a human is 37.

Thus, for a human of approx 60 Kg a 100 mg/Kg dose in rat would equate to a human dose of about 1000 mg. Human doses of greater than 300 mg/day, through 400 mg/day in 100 mg intervals (namely through 500, 600, 700, 800, 900, 1000, 1100, 1200, 1300 and 1400 mg) to as much as 2000 mg/day are envisaged based on dose escalating studies with CBD (Example 2).

Experimental Setup:

Five 6 L Perspex tanks with lids were placed on a single bench with dividers between them. Closed-circuit television (CCTV) cameras were mounted onto the dividers to observe rat behaviour. Sony Topica CCD cameras (Bluecherry, USA) were linked via BNC cables to a low-noise PC via Brooktree digital capture cards (Bluecherry, USA). Zoneminder (http://www.zoneminder.com) software was used to monitor rats, start and end recordings and manage video files. In-house Linux scripts were used to encode video files into a suitable format for further offline analysis using The Observer (Noldus Technologies).

PTZ Model:

A range of doses of PTZ (50-100 mg/kg body weight) were used to determine the best dose for induction of seizures (data not shown). As a result, a dose of 80 mg/kg injected intra-peritoneally (IP; stock solution 50 mg/ml in 0.9% saline) were used to screen the CBD/SAEDs combinations.

Experimental Protocols

On the day of testing, isolated CBD was administered via intra-peritoneal (i.p.) injection at a dose of 100 mg/kg alongside animals that were injected with a matched volume of the cannabinoid vehicle (2:1:17 ethanol:Cremophor: 0.9% w/v NaCl solution), which served as the negative control group. Animals were then observed for 1 hour, after which time they received an IP injection of 80 mg/kg PTZ. Negative vehicle controls were performed in parallel with cannabinoid-dosed subjects. After receiving a dose of PTZ, animals were observed and videoed to determine the severity of seizure and latency to several seizure behaviour types (see In vivo analysis, below). Animals were filmed for half an hour after last sign of seizure, and then returned to their cage.

In Vivo Analysis:

Animals were observed during experimental procedures, but all analysis was performed offline on recorded video files using The Observer behavioural analysis software (Noldus, Netherlands). A seizure severity scoring system was used to determine the levels of seizure experienced by subjects (Pohl & Mares, 1987). All signs of seizure were detailed for all animals.

TABLE 1.1

Seizure severity scoring scale, adapted from Pohl & Mares, 1987.

| Seizure score | Behavioural expression | Righting reflex |
| --- | --- | --- |
| 0 | No changes to behaviour | Preserved |
| 0.5 | Abnormal behaviour (sniffing, excessive washing, orientation) | Preserved |
| 1 | Isolated myoclonic jerks | Preserved |
| 2 | Atypical clonic seizure | Preserved |
| 3 | Fully developed bilateral forelimb clonus | Preserved |
| 3.5 | Forelimb clonus with tonic component and body twist | Preserved |
| 4 | Tonic-clonic seizure with suppressed tonic phase | Lost |
| 5 | Fully developed tonic-clonic seizure | Lost |
| 6 | Death | |

Latency from injection of PTZ to Specific Indicators of Seizure Development:

The latency (in seconds) from injection of PTZ to first myoclonic jerk (FMJ; score of 1), and to the animal attaining "forelimb clonus with tonic component and body twist" (score of 3.5) were recorded. FMJ is an indicator of the onset of seizure activity, whilst >90% of animals developed scores of 3.5, and so is a good marker of the development of more severe seizures. Data are presented as the mean±S.E.M. within an experimental group.

Maximum Seizure Severity:

This is given as the median value for each experimental group based on the scoring scale below.

Percentage Mortality:

The percentage of animals within an experimental group that died as a result of PTZ-induced seizures. Note that the majority of animals that developed tonic-clonic seizures (scores of 4 and 5) died as a result, and that a score of 6 (death) automatically denotes that the animal also experienced tonic-clonic seizures.

Seizure Duration:

The time (in seconds) from the first sign of seizure (typically FMJ) to either the last sign of seizure or, in the case of subjects that died, the time of death—separated into animals that survived and those that did not. This is given as the mean f S.E.M. for each experimental group.

Statistics

For measures of latency and severity, one way analysis of variance (ANOVA) was performed on the test groups to detect overall combinational effects of CBD and SAEDs ($p \leq 0.05$ considered significant).

Significant ANOVA results were followed by post hoc tests to test differences between vehicle and drug groups (Tukey's test, $p \leq 0.05$ considered significant).

Results

From FIG. 1 it can be seen that the addition of CBD to the SAED valproate has an effect on reducing the percentage mortality and the incidence of tonic-clonic seizures. It is also shown that the combination of CBD and the higher dose of valproate is more effective at increasing the amount of time that the animal was seizure free.

FIG. 2 demonstrates that the combination of CBD and valproate was able to increase the latency to onset of seizure at all dose ranges, in addition it decreased the overall duration of the seizure.

The data shown in FIG. 3 demonstrates that the combination of CBD with the SAED ethosuximide was also effective at reducing the severity and mortality of the seizures. It also at the higher dose of ethosuximide was able to increase the latency to onset of the seizures.

Conclusion

The data demonstrated in this Example clearly shows that the combination of CBD with a SAED which has a mechanism of action involving sodium or calcium channels is of value when treating generalised seizures.

Example 2

The Use of the Phytocannabinoid CBD in Combination with a Standard Anti-Epileptic Drug (SAED) in the Pilocarpine Model of (Temporal Lobe) Epilepsy Methodology Isolated CBD was injected intra-peritoneally (IP) in the standard vehicle (1:1:18 ethanol:Cremophor:0.9% w/v NaCl) at doses of 50, 100 and 200 mg/kg alongside animals that received vehicle alone at a matched volume. 15 minutes later methylscopolamine (1 mg/kg; to reduce peripheral muscarinic effects of pilocarpine) was administered followed, 45 minutes later by pilocarpine (380 mg/kg, IP) administration.

Results

FIG. 4 demonstrates the anti-convulsant effects of a combination of CBD and valproate in the pilocarpine model of epilepsy. These data show that the combination of the CBD and valproate was able to increase the latency of onset of the seizure.

It can be seen from the data illustrated in FIG. 5 that in addition to increasing the latency of onset of the seizure the combination of CBD and valproate was able to decrease mortality and the percentage of tonic-clonic seizures.

Table 2.1 below describes the data in more detail.

TABLE 2.1

Anti-convulsant effects of CBD and valproate in the pilocarpine model of epilepsy

| | Seizure Measure | CBD Effects | Valproate Effects | CBD in Combination with Valproate Effects |
|---|---|---|---|---|
| ALL EPISODES | Mean number of episodes | | ** | # |
| | Mean time spent in episodes | | * | |
| | Mean duration of episodes | | * | |
| | Mean severity of episodes | * | ** | |
| | Percentage ≥3 episodes | | | # |
| | Percentage episode free | | | ** |
| EPISODE 1 | Latency | | | ** |
| | Duration | | | |
| | Severity | | * | |
| EPISODE 2 | Latency | | | # |
| | Duration | | | # |
| | Severity | * | | |

Key: # = p < 0.01;
* = p < 0.05;
** = p < 0.01

The table above clearly shows some of the advantages of using a combination of the two compounds.

Table 2.2 below describes the effect of using the phytocannabinoid CBD in combination with yet a further SAED, phenobarbital, in the pilocarpine model of epilepsy.

TABLE 2.2

Effects of CBD and phenobarbital on the pilocarpine model of epilepsy

| CBD (mg/kg) | Phenobarbitol (mg/kg) | Seizure free (%) | Onset latency (s) |
|---|---|---|---|
| 0 | 0 | 0 | 750 |
| 100 | 0 | 0 | 500 |
| 0 | 10 | 25 | 800 |
| 100 | 10 | 25 | 750 |
| 0 | 20 | 55 | 900 |
| 100 | 20 | 55 | 930 |
| 0 | 40 | 75 | 1800 |
| 100 | 40 | 85 | 900 |

In contrast to the valproate combination data, this result demonstrate the selective nature of the combinations which is likely attributed to the different mechanisms of actions of these SAED's.

OVERALL CONCLUSION

The data demonstrated in the above Examples shows that the combination of CBD with standard anti-epileptic drugs acting via sodium or calcium channels may be beneficial in the treatment of different types of epilepsy. This finding is of great significance to the many epilepsy sufferers whose condition is refractory to existing medication.

The invention claimed is:

1. A method for treating epilepsy in a subject in need thereof, comprising:
    administering to the subject cannabidiol (CBD), at a dose of greater than 300 mg/day, in combination with valproate.
2. The method of claim 1, wherein the epilepsy is a generalized seizure or a temporal lobe seizure.
3. The method of claim 1, wherein the epilepsy is refractory to existing medication.
4. The method of claim 1, wherein the CBD is administered with one or more other therapeutically effective phytocannabinoids.
5. The method of claim 4, wherein the one or more other therapeutically effective phytocannabinoids is THCV and/or CBDV.
6. The method of claim 1, wherein the CBD is an isolated phytocannabinoid.
7. The method of claim 1, wherein the CBD is in a form of a botanical drug substance.
8. The method of claim 1, wherein CBD and valproate are administered in a ratio of valproate to CBD of at least 1:1.
9. The method of claim 1, wherein CBD and valproate are administered in a ratio of valproate to CBD of no more than 3.5:1.
10. The method of claim 1, wherein CBD and valproate are administered in a ratio of valproate to CBD in the range of 3.5:1 to 1:1.
11. The method of claim 1, wherein the administration of CBD and valproate results in a lower percentage of tonic-clonic seizures compared to the administration of either CBD or valproate alone.
12. The method of claim 1, wherein the administration of CBD and valproate results to a patient population results in a higher percentage of seizure-free patients compared to the administration of either CBD or valproate alone.

* * * * *